(12) United States Patent
Wang et al.

(10) Patent No.: US 9,650,369 B2
(45) Date of Patent: May 16, 2017

(54) ANTI-MIGRATION AND ANTI-INVASION THIAZOLE ANALOGS FOR TREATMENT OF CELLULAR PROLIFERATIVE DISEASE

(71) Applicant: XAVIER UNIVERSITY OF LOUISIANA, New Orleans, LA (US)

(72) Inventors: Guangdi Wang, New Orleans, LA (US); Quan Jiang, New Orleans, LA (US); Qiu Zhong, New Orleans, LA (US); Qiang Zhang, New Orleans, LA (US); Shilong Zheng, New Orleans, LA (US)

(73) Assignee: XAVIER UNIVERSITY OF LOUISIANA, New Orleans, LA (US)

( * ) Notice: Subject to any disclaimer, the term of this patent is extended or adjusted under 35 U.S.C. 154(b) by 0 days.

(21) Appl. No.: 14/431,789

(22) PCT Filed: Sep. 27, 2013

(86) PCT No.: PCT/US2013/062302
§ 371 (c)(1),
(2) Date: Mar. 27, 2015

(87) PCT Pub. No.: WO2014/052831
PCT Pub. Date: Apr. 3, 2014

(65) Prior Publication Data
US 2015/0274714 A1 Oct. 1, 2015

Related U.S. Application Data

(60) Provisional application No. 61/707,391, filed on Sep. 28, 2012.

(51) Int. Cl.
| | | |
|---|---|---|
| *C07D 417/12* | (2006.01) | |
| *C07D 277/18* | (2006.01) | |
| *C07D 277/44* | (2006.01) | |
| *A61K 31/426* | (2006.01) | |
| *A61K 31/427* | (2006.01) | |
| *C07D 277/40* | (2006.01) | |
| *C07D 277/46* | (2006.01) | |
| *A61K 45/06* | (2006.01) | |
| *A61K 31/4439* | (2006.01) | |
| *C07D 277/52* | (2006.01) | |

(52) U.S. Cl.
CPC .......... *C07D 417/12* (2013.01); *A61K 31/426* (2013.01); *A61K 31/427* (2013.01); *A61K 31/4439* (2013.01); *A61K 45/06* (2013.01); *C07D 277/40* (2013.01); *C07D 277/44* (2013.01); *C07D 277/46* (2013.01); *C07D 277/52* (2013.01)

(58) Field of Classification Search
CPC .................................................. C07D 227/18
See application file for complete search history.

(56) References Cited

U.S. PATENT DOCUMENTS

| | | | | |
|---|---|---|---|---|
| 4,379,156 A | * | 4/1983 | Islip ..................... | C07D 277/58 514/370 |
| 7,285,567 B2 | * | 10/2007 | Rossignol ............ | C07D 277/46 514/365 |
| 7,396,842 B2 | * | 7/2008 | Fujiwara .............. | C07D 231/12 514/235.5 |
| 8,163,783 B2 | | 4/2012 | Yun et al. | |
| 2008/0312435 A1 | * | 12/2008 | Saito .................... | C07D 213/75 544/133 |
| 2015/0274714 A1 | * | 10/2015 | Wang .................... | A61K 45/06 514/342 |

FOREIGN PATENT DOCUMENTS

| | | | | |
|---|---|---|---|---|
| JP | 63203672 A | * | 8/1988 | |
| JP | WO 2006051704 A1 | * | 5/2006 | .......... C07D 213/75 |
| WO | 03103655 A1 | | 12/2003 | |
| WO | 2007140385 A2 | | 12/2007 | |

OTHER PUBLICATIONS

Beer, et al. Tetrahedron (1979), 35 (9), 1199-203.*
Yavari et al. Phosphorus, Sulfur and Silicon and the Related Elements (2011), 186(1), 134-139 (published online Jan. 13, 2011).*
Azaryan, Azerbaidzhanskii Khimicheskii Zhurnal (1967), 20(2), 135-140.*
Ramachandraiah et al Indian Journal of Chemistry, Section B: Organic Chemistry Including Medicinal Chemistry (1985) 24B(8), 808-810.*
Hansell et al. Acta Cryst. (1996), C52, pp. 136-139.*
Andreani et al. Collect. Czech. Chem. Commun., vol. 64 (1999), 299-312.*
International Search Report from corresponding PCT/US2013/062302, mailed Jan. 27, 2014.
Cancer and Metastasis Reviews 19: pp. 193-204, 2000, Kluwer Academic Publishers, "Observations on the antiquity of cancer and metastasis".
Chambers et al., "Dissemination and Growth of Cancer Cells in Metastatic Sites", Nature Reviews, vol. 2, Aug. 2002, pp. 563-572.
Chambers et al., "Clinical Targets for Anti-Metastasis Therapy", Advances in Cancer Research, London, Ontario, Canada, pp. 91-121.
Epstein, "Maintenance Therapy to Suppress Micrometastasis: The New Challenge for Adjuvant Cancer Treatment", Clin Cancer Res, Aug. 1, 2005, pp. 5337-5341.

(Continued)

*Primary Examiner* — Nyeemah A Grazier
(74) *Attorney, Agent, or Firm* — McBee Moore Woodward & Vanik IP, LLC

(57) ABSTRACT

Thiazole analog compounds and their pharmaceutically acceptable salts are disclosed, including pharmaceutical compositions comprising the thiazole analog compounds, either alone or in combination with at least one additional therapeutic agent, and/or with a pharmaceutically acceptable carrier. Methods of using the thiazole analog compounds, either alone or in combination with at least one additional therapeutic agent, in the prophylaxis or treatment of cellular proliferative diseases, such as cancer, are also disclosed.

20 Claims, 8 Drawing Sheets

(56) References Cited

OTHER PUBLICATIONS

Fidler, "The pathogenesis of cancer metastasis: the 'seed and soil' hypothesis revisited", Nature reviews, vol. 3, Jun. 2003, pp. 1-6.
Hanahan et al., "Hallmarks of Cancer: The Next Generation", Cell 144, Mar. 4, 2011, The Swiss Institute for Experimental Cancer Research (ISREC), School of Life Sciences, EPFL, Lausanne, Switzerland, The Department of Biochemistry & Biophysics, UCSF, San Francisco, CA, Whitehead Institute for Biomedical Research, Ludwig/MIT Center for Molecular Oncology, and MIT Department of Biology, Cambridge, MA, pp. 646-674.
Jordan et al., "Microtubules as a Target for Anticancer Drugs", Nature Reviews, vol. 4, Apr. 2004, pp. 253-265.
Overall et al., "Strategies in Cancer: for MMP Inhibition Innovations for the Post-Trial Era", Nature Reviews, vol. 2, Sep. 2002, pp. 657-672.

* cited by examiner

ANTI-MIGRATION AND ANTI-INVASION THIAZOLE ANALOGS FOR TREATMENT OF CELLULAR PROLIFERATIVE DISEASE

CROSS-REFERENCE TO RELATED APPLICATIONS

This application is a 371 National Phase of PCT/US2013/062302, filed 27 Sep. 2013, which claims the benefit of U.S. Provisional Patent Application No. 61/707,391, filed 28 Sep. 2012, which are hereby incorporated by reference in their entireties.

STATEMENT REGARDING FEDERALLY SPONSORED RESEARCH OR DEVELOPMENT

Not applicable.

BACKGROUND

1. Field

The present disclosure relates to new thiazole analog compounds and their pharmaceutically acceptable salts; pharmaceutical compositions comprising the new thiazole analog compounds, either alone or in combination with at least one additional therapeutic agent, with a pharmaceutically acceptable carrier; and uses of the new thiazole analog compounds, either alone or in combination with at least one additional therapeutic agent, in the prophylaxis or treatment of cellular proliferative diseases, such as cancer, and in particular cancer presenting as metastatic tumors.

2. Description of Related Art

Metastasis is the major cause of death in cancer patients: nearly 90% mortality has been attributed to metastatic spread of the disease rather than to the primary tumor. See, e.g., Chambers, A. F.; Groom, A. C.; MacDonald, I. C. Dissemination and growth of cancer cells in metastatic sites. *Nature Rev. Cancer* 2002; 2:563-572; Fidler, I. J. The pathogenesis of cancer metastasis: the 'seed and soil' hypothesis revisited. *Nature Rev Cancer.* 2003; 3:453-458; and Hanahan, D.; Weinberg, R. A. Hallmarks of cancer: the next generation. *Cell.* 2011; 144:646-674. Decades of intensive research have focused on the search for therapeutic solutions targeting cancer cell migration and invasion, and angiogenesis. See Weiss, L. Metastasis of cancer: a conceptual history from antiquity to the 1990s. *Cancer Metastasis Rev.* 2000; 19:193-383.

Metastasis is a complex process, involving multiple steps that include cancer cell motility, intravasation, transit and survival in the circulation, extravasation, and growth at a new site. While in theory, inhibition of any of these metastatic stages will prevent the formation of tumors at remote sites, clinically the window of opportunity to block metastasis may not be as optimal as one might hope for. See Chambers, A. F.; MacDonald, I. C.; Schmidt, E. E; Morris, V. L.; Groom, A. C. Clinical targets for anti-metastasis therapy. *Adv Cancer Res.* 2000; 79:91-121. For example, stages involving cancer cell survival in the circulation, arrest and extravasation, may not be ideal targets for development of therapeutic solutions, as these processes appear to occur relatively fast, in large numbers, and are less vulnerable to drug interference. On the other hand, growth of cancer cells in secondary sites takes much longer to cause irreversible damage, thus offering a broader time window for prevention of metastasis. See Chambers 2000, and Epstein, R. J. Maintenance therapy to suppress micrometastasis: the new challenge for adjuvant cancer treatment. *Clin Cancer Res.* 2005; 11:5337-5341.

Small molecule drugs, such as matrix metalloproteinases (MMP) inhibitors (see Overall, C. M.; Lopez-Otin, C. Strategies for MMP inhibition in cancer: innovations for the post-trial era. *Nature Rev. Cancer* 2002; 2:657-672) and tubulin targeted inhibitors (see Jordan, M. A.; Wilson, L. Microtubules as a target for anticancer drugs. *Nat. Rev. Cancer* 2004; 4:253-265), have been developed to block metastasis. So far these drugs have had only limited clinical success. Most chemotherapies target cancer cell proliferation as a means to inhibit dissemination, leading to toxicity to healthy cells, as well as acquired resistance in cancer cells. The metastasis modifying processes, however, may be more effectively influenced by long term treatment of non-cytotoxic drugs such as protease inhibitors, chemokine antagonists, kinase blockers, adhesion modifiers, and anti-inflammation agents. See Epstein, 2005. The search for improved, more potent, and less toxic drugs for metastasis intervention remains an ongoing effort.

For the foregoing reasons, there is therefore a great need in the art for new drugs capable of treating cellular proliferative diseases, which are especially suited for disrupting the metastatic processes of cancerous cells.

The solution to this technical problem is provided by the embodiments characterized in the claims.

BRIEF SUMMARY OF THE INVENTION

To overcoming the shortcomings in the art and to provide novel compounds suitable for the treatment of cellular proliferative diseases, a series of novel thiazole analogs, based on the structural motif of compound 5a was designed and synthesized. The in vitro efficacies of these novel thiazole compounds were evaluated in two models of invasive and metastatic cancer cell lines for their ability to suppress cell motility. The results demonstrate the potential utility of the most potent thiazole analogs as anti-metastatic and non-cytotoxic therapeutic agents for the treatment of cellular proliferative diseases.

Thus, in one aspect, the present invention relates to new thiazole analog compounds and their pharmaceutically acceptable salts; pharmaceutical compositions comprising the new thiazole analog compounds, either alone or in combination with at least one additional therapeutic agent, with a pharmaceutically acceptable carrier; and uses of the new thiazole analog compounds, either alone or in combination with at least one additional therapeutic agent, in the prophylaxis or treatment of cellular proliferative diseases, such as cancer, and in particular cancer presenting as metastatic tumors.

In another embodiment, the invention relates to novel thiazole-derived compounds that have been discovered to have potent inhibitory effects on cancer cell migration and invasion, with $IC_{50}$ values in the submicromolar range. Moreover, these analogs exhibit low or negligible cytotoxicity, after incubation with invasive breast cancer and cervical cancer cells for two weeks, allowing the cells to form robust colonies. Thus, these thiazole analogs can be useful in the treatment of metastatic tumors with minimal toxicity to healthy organs and tissues.

In accordance with another embodiment of the invention, methods of manufacturing or preparing the disclosed novel thiazole analog compounds are presented.

Another embodiment of the present invention relates to methods of using the thiazole analogs for the treatment of particular cancers, including breast cancer, and cancer cells that are invasive in nature.

Another embodiment of the present invention relates to methods of using the thiazole analogs for the treatment of non-small cell lung cancers.

Further, embodiments of the present invention may be utilized to treat a wide variety of cancers. For example, particular embodiments of the invention can be utilized in the treatment of the following carcinomas: Ovarian carcinoma (serous cystadenocarcinoma, mucinous cystadenocarcinoma, endometrioid carcinoma), Ovarian granulosa cell tumor, Fallopian tube adenocarcinoma, Peritoneal carcinoma, Uterine (endometrial) adenocarcinoma, sarcomatoid carcinoma, Cervical squamous cell carcinoma, Endocervical adenocarcinoma, Vulvar carcinoma, Breast carcinoma, primary and metastatic (ductal carcinoma, mucinous carcinoma, lobular carcinoma, malignant phyllodes tumor), Head and neck carcinoma, Oral cavity carcinoma including tongue, primary and metastatic, Esophageal carcinoma, squamous cell carcinoma and adenocarcinoma, Gastric adenocarcinoma, malignant lymphoma, GIST, Primary small bowel carcinoma, Colonic adenocarcinoma, primary and metastatic (adenocarcinoma, mucinous carcinoma, large cell neuroendocrine carcinoma, colloid carcinoma), Appendiceal adenocarcinoma, Colorectal carcinoma, Rectal carcinoma, Anal carcinoma (squamous, basaloid), Carcinoid tumors, primary and metastatic (appendix, small bowel, colon), Pancreatic carcinoma, Liver carcinoma (hepatocellular carcinoma, cholangiocarcinoma), Metastatic carcinoma to the liver, Lung cancer, primary and metastatic (squamous cell, adenocarcinoma, adenosquamous carcinoma, giant cell carcinoma, nonsmall cell carcinoma, NSCLC, small cell carcinoma neuroendocrine carcinoma, large cell carcinoma, bronchoalveolar carcinoma), Renal cell (kidney) carcinoma, primary and metastatic, Urinary bladder carcinoma, primary and metastatic, Prostatic adenocarcinoma, primary and metastatic, Brain tumors, primary and metastatic (glioblastoma, multiforme, cerebral neuroectodermal malignant tumor, neuroectodermal tumor, oligodendroglioma, malignant astrocytoma), Skin tumors (malignant melanoma, sebaceous cell carcinoma), Thyroid carcinoma (papillary and follicular), Thymic carcinoma, Shenoidal carcinoma, Carcinoma of unknown Primary, Neuroendocrine carcinoma, Testicular malignancies (seminoma, embryonal carcinoma, malignant mixed tumors), and others.

In another embodiment, the thiazole analogs of the present disclosure can be used to treat the following malignant lymphomas, for example: Large cell malignant lymphoma, Small cell lymphoma, Mixed large and small cell lymphoma, Malt lymphoma, Non Hodgkin malignant lymphoma, T cell malignant lymphoma, and others.

Further still, embodiments of the invention may use the novel thiazole analogs to treat the following leukemias, for example: AML-acute myelogenous leukemia, ALL-acute lymphoblastic leukemia, chronic lymphocytic leukemia, Multiple myeloma, Myelodysplastic syndromes-MDS, MDS with myelofibrosis, Waldenstrom's macroglobulinemia, and others.

Also, sarcomas such as the following may be treated with embodiments of the presently disclosed thiazole analogs: Leiomyosarcoma (uterine sarcoma), GIST-gastrointestinal stromal tumor, primary and metastatic (stomach, small bowel, Colon), Liposarcoma, Myxoid sarcoma, Chondrosarcoma, Osteosarcoma, Ewings sarcoma/PNET, Neuroblastoma, Malignant peripheral nerve sheath tumor, Spindle cell carcinoma, Embryonal rhabdomyosarcoma, Mesothelioma, and others.

Thus, it can easily be recognized that the presently disclosed novel thiazole analog compounds and their pharmaceutically acceptable salts—or pharmaceutical compositions comprising the new thiazole analog compounds, either alone or in combination with at least one additional therapeutic agent, with a pharmaceutically acceptable carrier—are useful in the treatment of all types of cellular proliferative diseases, such as the multitude of cancers aforementioned.

It is a further object of the invention to provide a composition comprising one or more of the disclosed novel thiazole compounds, used in combination with one or more of an existing chemotherapeutic agent, for minimizing or delaying tumor metastasis. In this aspect, the novel thiazole analogs used in combination with a known chemotherapeutic agent, will produce beneficial anti-metastatic compositions and treatments that demonstrate superior efficacy when compared to treatments utilizing only the known chemotherapeutic agent.

Another embodiment of this invention is a kit, comprising a composition containing one or more of the disclosed novel thiazole compounds, used alone or in combination with an existing chemotherapeutic agent, and a delivery mechanism. The delivery mechanism would be any type of device or system known to those of skill in the art to be suitable for the administration of the composition to a human or animal subject, e.g. syringes, intravenous bags and assemblages, etc. The kit would be useful for minimizing the time and inefficiencies that are created by doctors having to individually assemble the components necessary for delivering a treatment to a patient. Consequently, the kit embodiment of the invention could be utilized as an off the shelf, or prepackaged, treatment protocol. These types of prepackaged drug delivery systems are of particular importance in understaffed hospitals or developing countries, in which there is not a sufficient level of medical expertise available to accurately determine the appropriate dosage of a composition comprising the novel thiazole analog on a fast and consistent basis. The kits therefore provide a fast and accurate method by which to utilize the disclosed novel thiazole analogs.

In other embodiments, the particular thiazole analog can be any of the individually listed compounds recited in the below "Compound List and Identifications" section. Furthermore, any pharmaceutically acceptable salt of the individually listed compounds are also part of the present invention. Further still, as aforementioned, a composition comprising any combination of the below listed thiazole analogs is also a part of the present invention. Said composition can include any pharmaceutically acceptable carrier, as well as a further therapeutic agent, for example a known chemotherapeutic agent.

In another aspect, the present invention provides methods for treating cellular proliferative diseases, such as cancer, in a human or animal subject in need of such treatment, comprising administering to said subject an amount of a thiazole compound, selected from the below "Compound List and Identifications," which is effective to reduce or prevent cellular proliferation in the subject. Said method may also include administering any of the listed thiazole compounds in a composition, which comprises a pharmaceutically acceptable carrier, as well as a further therapeutic agent. The therapeutic agent administered along with one or more of the disclosed thiazole analogs may be any agent known in the art to be beneficial for the treatment of cancer, such as chemotherapeutic agents, radiation, immunotherapeutic agents, etc.

In one aspect, the present disclosure provides compounds of Formula (I):

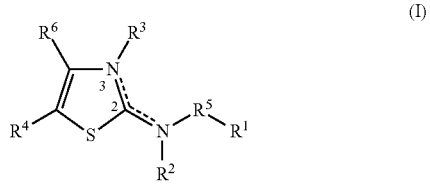

wherein
- $R^1$ is thiophen-2-yl, furan-2-yl, 4-chlorophenyl, 4-bromophenyl, 3,4,5-trimethoxyphenyl, 3,4-dimethoxyphenyl, pyridin-3-yl, pyridin-4-yl, phenyl, cyclopentyl, cyclohexyl, n-pentyl, n-undecyl, phenyl, 4-methylphenyl, methoxyphenyl, dimethoxyphenyl at any two positions 2-6, trimethoxyphenyl at any three positions 2-6, $C_1$-$C_{20}$ alkyl, aryl, $C_3$-$C_7$ cycloalkyl, heterocyclyl, aryl ($C_1$-$C_6$ alkyl), or heterocyclyl ($C_1$-$C_6$ alkyl);
- $R^2$ is hydrogen, methyl, ethyl, n-propyl, n-butyl, n-hexyl, n-dodecyl, $C_1$-$C_{12}$ alkyl, allyl, propynyl, or is absent;
- $R^3$ is methyl, ethyl, n-propyl, n-butyl, n-hexyl, n-dodecyl, $C_1$-$C_{12}$ alkyl, allyl, propynyl, or is absent;
- $R^4$ is hydrogen, methyl, tolyl, methoxyphenyl, $C_1$-$C_{12}$ alkyl, or aryl;
- $R^5$ is hydrogen, —C(=O)— or —S(=O)$_2$—;
- $R^6$ hydrogen, methyl, cyclopropyl, phenyl, xylyl, chlorophenyl, bromophenyl, fluorophenyl, bis(trifluoromethyl)phenyl, trimethoxy phenyl, cyclopropyl, $C_2$-$C_{20}$ alkyl, $C_3$-$C_7$ cycloalkyl, aryl ($C_6$-$C_{10}$), or aromatic heterocyclyl ($C_3$-$C_9$); and
- the dashed lines represent optional double bonds;

and wherein
- if $R^2$ is absent, then the optional double bond between the amino nitrogen and position 2 of the thiazole ring is present; and
- if $R^3$ is absent, then the optional double bond between positions 2 and 3 of the thiazole ring is present, and salts thereof.

In a favored aspect of Formula (I), $R^1$ is phenyl, methoxyphenyl at any position 2-6, dimethoxyphenyl at any two positions 2-6, trimethoxyphenyl at any three positions 2-6; $R^5$ is —C(=O)—; and $R^7$ is phenyl, xylyl, or trimethoxyphenyl at any three positions 2-6, or a salt thereof.

In another favored aspect of Formula (I), $R^1$ is phenyl; $R^2$ is hydrogen, methyl, or is absent; $R^4$ is hydrogen or methyl; $R^5$ is —C(=O)—; and $R^6$ is phenyl, xylyl, cyclopropyl, chlorophenyl, bromophenyl, or bis(trifluoromethyl)phenyl, or a salt thereof.

In another aspect, the compound is selected from the group consisting of: 2-Amino-4-phenylthiazole, 2-Amino-4-(2,4-dimethylphenyl)thiazole, N-(4-Phenylthiazol-2-yl)thiophene-2-carboxamide, N-(4-Phenylthiazol-2-yl)furan-2-carboxamide, 4-Chloro-N-(4-phenylthiazol-2-yl)benzamide, 4-Bromo-N-(4-phenylthiazol-2-yl)benzamide, 3,4,5-Trimethoxy-N-(4-phenylthiazol-2-yl)benzamide, N-(4-(2,4-Dimethylphenyl)thiazol-2-yl)thiophene-2-carboxamide, 3,4-Dimethoxy-N-(4-phenylthiazol-2-yl)benzamide, N-(4-Phenylthiazol-2-yl)nicotinamide, N-(4-Phenylthiazol-2-yl)isonicotinamide, N-(4-Phenylthiazol-2-yl)benzamide, N-(4-Phenylthiazol-2-yl)cyclopentanecarboxamide, N-(4-Phenylthiazol-2-yl)cyclohexanecarboxamide, N-(4-Phenylthiazol-2-yl)hexanamide, N-(4-Phenylthiazol-2-yl)dodecanamide, N-(4-(2,4-dimethylphenyl)thiazol-2-yl)benzamide, 4-Bromo-N-methyl-N-(4-phenylthiazol-2-yl)benzamide, N-(4-(2,4-dimethylphenyl)thiazol-2-yl)-N-methylthiophene-2-carboxamide, 3,4-Dimethoxy-N-methyl-N-(4-phenylthiazol-2-yl)benzamide, N-Ethyl-N-(4-phenylthiazol-2-yl)furan-2-carboxamide, N-Methyl-N-(4-phenylthiazol-2-yl)benzamide, N-Methyl-N-(4-phenylthiazol-2-yl)cyclopentanecarboxamide, N-Methyl-N-(4-phenylthiazol-2-yl)cyclohexanecarboxamide, N-Methyl-N-(4-phenylthiazol-2-yl)hexanamide, N-Methyl-N-(4-phenylthiazol-2-yl)dodecanamide, N-(3-Methyl-4-phenylthiazol-2(3H)-yliene)thiophene-2-carboxamide, N-(3-Methyl-4-phenylthiazol-2(3H)-yliene) furan-2-carboxamide, 4-Chloro-N-(3-methyl-4-phenylthiazol-2(3H)-ylidene)benzamide, 4-Bromo-N-(3-methyl-4-phenylthiazol-2(3H)-yliene)benzamide, 3,4,5-Trimethoxy-N-(3-methyl-4-phenylthiazol-2(3H)-yliene)benzamide, N-(4-(2,4-dimethylphenyl)-3-methylthiazol-2(3H)-yliene)thiophene-2-carboxamide, 3,4-Dimethoxy-N-(3-methyl-4-phenylthiazol-2(3H)-yliene)benzamide, N-(3-Methyl-4-phenylthiazol-2(3H)-yliene)nicotinamide, N-(3-Ethyl-4-phenylthiazol-2(3H)-yliene)thiophene-2-carboxamide, N-(3-Methyl-4-phenylthiazol-2(3H)-yliene)benzamide, N-(4-(2,4-Dimethylphenyl)-3-methylthiazol-2(3H)-yliene)-benzamide, N-(4-(2,4-Dimethylphenyl)-3-ethylthiazol-2(3H)-ylidene)benzamide, N-(4-(2,4-Dimethylphenyl)-3-propylthiazol-2(3H)-ylidene)benzamide, N-(3-Butyl-4-(2,4-dimethylphenyl)thiazol-2(3H)-ylidene)benzamide, N-(4-(2,4-Dimethylphenyl)-3-hexylthiazol-2(3H)-ylidene)benzamide, N-(4-(2,4-Dimethylphenyl)-3-dodecylthiazol-2(3H)-ylidene)benzamide, N-(3-Allyl-4-(2,4-dimethylphenyl)thiazol-2(3H)-ylidene)benzamide, N-(4-(2,4-Dimethylphenyl)-3-(prop-2-yn-1-yl)thiazol-2(3H)-ylidene)benzamide, N-(4-(2,4-Dimethylphenyl)thiazol-2-yl)-N-(prop-2-yn-1-yl)benzamide, N-Ethyl-N-(4-phenylthiazol-2-yl)benzamide, N-(4-Phenyl-3-propylthiazol-2(3H)-ylidene)benzamide, N-(3-Allyl-4-phenylthiazol-2(3H)-ylidene)benzamide, N-(4-Phenyl-3-(prop-2-yn-1-yl)thiazol-2(3H)-ylidene)benzamide, N-(4-phenyl-3-ethylthiazol-2(3H)-ylidene)benzamide, N-(4-Phenylthiazol-2-yl)-N-propylbenzamide, N-(4-(2,4-Dimethylphenyl)thiazol-2-yl)benzenesulfonamide, N-(4-(2,4-Dimethylphenyl)-3-methylthiazol-2(3H)-ylidene) benzenesulfonamide, N-(4-(2,4-Dimethylphenyl)thiazol-2-yl)-N-methylbenzenesulfonamide, N-(4-Methylthiazol-2-yl)benzamide, N-(4-(2-Chlorophenyl)thiazol-2-yl) benzamide, N-(4-(3-Bromophenyl)thiazol-2-yl)benzamide, N-(4-(4-Bromophenyl)thiazol-2-yl)benzamide, N-(4-(3-Chlorophenyl)thiazol-2-yl)benzamide, N-(4-(3,5-Bis(trifluoromethyl)-phenyl)thiazol-2-yl)benzamide, N-(4-(3,4,5-Trimethoxyphenyl)thiazol-2-yl)benzamide, N-(5-Methyl-4-phenylthiazol-2-yl)benzamide, N-(4-(4-Fluorophenyl)-5-methylthiazol-2-yl)benzamide, N-(5-(p-Tolyl)thiazol-2-yl) benzamide, 4-Methoxy-N-(4-(3,4,5-trimethoxyphenyl) thiazol-2-yl)benzamide, 4-Chloro-N-(4-(3,4,5-trimethoxyphenyl)thiazol-2-yl)benzamide, 3,4-Dimethoxy-N-(4-(3,4,5-trimethoxyphenyl)thiazol-2-yl)benzamide, 2,4-Dimethoxy-N-(4-(3,4,5-trimethoxyphenyl)thiazol-2-yl) benzamide, 3,4,5-Trimethoxy-N-(4-(3,4,5-trimethoxyphenyl)thiazol-2-yl)benzamide, 2,3-Dimethoxy-N-(4-(3,4,5-trimethoxyphenyl)thiazol-2-yl)benzamide, 2-Methoxy-N-(4-(3,4,5-trimethoxyphenyl)thiazol-2-yl)benzamide, 3-Methoxy-N-(4-(3,4,5-trimethoxyphenyl)thiazol-2-yl)benzamide, N-(3,4-Dimethylthiazol-2(3H)-ylidene)

benzamide, N-(4-(2-Chlorophenyl)-3-methylthiazol-2(3H)-ylidene)benzamide, N-(4-(3-Bromophenyl)-3-methylthiazol-2(3H)-ylidene)benzamide, N-(4-(4-Bromophenyl)-3-methylthiazol-2(3H)-ylidene)benzamide, N-(4-(3-Chlorophenyl)-3-methylthiazol-2(3H)-ylidene)benzamide, N-(4-(3,5-Bis(trifluoromethyl)phenyl)-3-methylthiazol-2(3H)-ylidene)benzamide, N-(4-(3,4,5-Trimethoxyphenyl)-3-methylthiazol-2(3H)-yliene)-benzamide, N-(3,5-Dimethyl-4-phenylthiazol-2(3H)-ylidene)benzamide, N-(4-(4-Fluorophenyl)-3,5-dimethylthiazol-2(3H)-ylidene) benzamide, N-(3-Methyl-5-(p-toyl)thiazol-2(3H)-ylidene) benzamide, 4-Methoxy-N-(3-methyl-4-(3,4,5-trimethoxyphenyl)thiazol-2(3H)-ylidene)-benzamide, 4-Chloro-N-(3-methyl-4-(3,4,5-trimethoxyphenyl)thiazol-2(3H)-ylidene)benzamide, 3-Methoxy-N-(3-methyl-4-(3,4,5-trimethoxyphenyl)thiazol-2(3H)-ylidene)benzamide, N-(4-Cyclopropyl-3-methylthiazol-2(3H)-ylidene)benzamide, 3,4,5-Trimethoxy-N-(3-methyl-4-(3,4,5-trimethoxyphenyl) thiazol-2(3H)-ylidene) benzamide, N-(4-(2-Chlorophenyl)thiazol-2-yl)-N-methylbenzamide, N-(4-(3-Bromophenyl) thiazol-2-yl)-N-methylbenzamide, N-(4-(4-Bromophenyl)-thiazol-2-yl)-N-methylbenzamide, N-Methyl-N-(4-(3,4,5-trimethoxyphenyl)thiazol-2-yl)benzamide, N-(4-(4-Fluorophenyl)-5-methylthiazol-2-yl)-N-methylbenzamide, N-Methyl-N-(5-(p-tolyl)thiazol-2-yl)benzamide, 4-Methoxy-N-methyl-N-(4-(3,4,5-trimethoxyphenyl)thiazol-2-yl)benzamide, 3,4-Dimethoxy-N-methyl-N-(4-(3,4,5-trimethoxyphenyl)thiazol-2-yl)benzamide, 2,4-Dimethoxy-N-methyl-N-(4-(3,4,5-trimethoxyphenyl)thiazol-2-yl)benzamide, 3,4,5-Trimethoxy-N-methyl-N-(4-(3,4,5-trimethoxyphenyl)thiazol-2-yl)benzamide, 2,3-Dimethoxy-N-methyl-N-(4-(3,4,5-trimethoxy-phenyl)thiazol-2-yl) benzamide, 2-Methoxy-N-methyl-N-(4-(3,4,5-trimethoxyphenyl)thiazol-2-yl)benzamide, 3-Methoxy-N-methyl-N-(4-(3,4,5-trimethoxyphenyl)thiazol-2-yl) benzamide, and salts thereof.

Said compounds may be used in the treatment of a cellular proliferative disease, such as a cancer, including but not limited to metastatic cancer, breast cancer, and non-small cell lung cancer.

Said compounds may be used for inhibiting cell migration and/or inhibiting cell invasion.

Said compounds may be in a form of a product for oral delivery, said product form being selected from the group consisting of a concentrate, dried powder, liquid, capsule, pellet, and pill. Said compounds may be in a form of a product for parenteral, intravenous, intradermal, intramuscular, or subcutaneous administration. Said compounds and/or forms may further comprise at least one carrier, binder, diluent, or excipient.

Said compounds may be administered at from about 0.01 to about 40 mg/kg/day. Said compounds may further comprise a chemotherapeutic agent.

Compound List and Identifications

2-Amino-4-phenylthiazole is referred to as compound 2a.

2-Amino-4-(2,4-dimethylphenyl)thiazole is referred to as compound 2b.

N-(4-Phenylthiazol-2-yl)thiophene-2-carboxamide is referred to as compound 3a.

N-(4-Phenylthiazol-2-yl)furan-2-carboxamide is referred to as compound 3b.

4-Chloro-N-(4-phenylthiazol-2-yl)benzamide is referred to as compound 3c.

4-Bromo-N-(4-phenylthiazol-2-yl)benzamide is referred to as compound 3d.

3,4,5-Trimethoxy-N-(4-phenylthiazol-2-yl)benzamide is referred to as compound 3e.

N-(4-(2,4-Dimethylphenyl)thiazol-2-yl)thiophene-2-carboxamide is referred to as compound 3f.

3,4-Dimethoxy-N-(4-phenylthiazol-2-yl)benzamide is referred to as compound 3g.

N-(4-Phenylthiazol-2-yl)nicotinamide is referred to as compound 3h.

N-(4-Phenylthiazol-2-yl)isonicotinamide is referred to as compound 3i.

N-(4-Phenylthiazol-2-yl)benzamide is referred to as compound 3j.

N-(4-Phenylthiazol-2-yl)cyclopentanecarboxamide is referred to as compound 3k.

N-(4-Phenylthiazol-2-yl)cyclohexanecarboxamide is referred to as compound 3l.

N-(4-Phenylthiazol-2-yl)hexanamide is referred to as compound 3m.

N-(4-Phenylthiazol-2-yl)dodecanamide is referred to as compound 3n.

N-(4-(2,4-dimethylphenyl)thiazol-2-yl)benzamide is referred to as compound 3o.

4-Bromo-N-methyl-N-(4-phenylthiazol-2-yl)benzamide is referred to as compound 4a.

N-(4-(2,4-dimethylphenyl)thiazol-2-yl)-N-methylthiophene-2-carboxamide is referred to as compound 4b.

3,4-Dimethoxy-N-methyl-N-(4-phenylthiazol-2-yl)benzamide is referred to as compound 4c.

N-Ethyl-N-(4-phenylthiazol-2-yl)furan-2-carboxamide is referred to as compound 4d.

N-Methyl-N-(4-phenylthiazol-2-yl)benzamide is referred to as compound 4e.

N-Methyl-N-(4-phenylthiazol-2-yl)cyclopentanecarboxamide is referred to as compound 4f.

N-Methyl-N-(4-phenylthiazol-2-yl)cyclohexanecarboxamide is referred to as compound 4g.

N-Methyl-N-(4-phenylthiazol-2-yl)hexanamide is referred to as compound 4h.

N-Methyl-N-(4-phenylthiazol-2-yl)dodecanamide is referred to as compound 4i.

N-(3-Methyl-4-phenylthiazol-2(3H)-yliene)thiophene-2-carboxamide is referred to as compound 5a.

N-(3-Methyl-4-phenylthiazol-2(3H)-yliene)furan-2-carboxamide is referred to as compound 5b.

4-Chloro-N-(3-methyl-4-phenylthiazol-2(3H)-ylidene)benzamide is referred to as compound 5c.

4-Bromo-N-(3-methyl-4-phenylthiazol-2(3H)-yliene)benzamide is referred to as compound 5d.

3,4,5-Trimethoxy-N-(3-methyl-4-phenylthiazol-2(3H)-yliene)benzamide is referred to as compound 5e.

N-(4-(2,4-dimethylphenyl)-3-methylthiazol-2(3H)-yliene) thiophene-2-carboxamide is referred to as compound 5f.

3,4-Dimethoxy-N-(3-methyl-4-phenylthiazol-2(3H)-yliene) benzamide is referred to as compound 5g.

N-(3-Methyl-4-phenylthiazol-2(3H)-yliene)nicotinamide is referred to as compound 5h.

N-(3-Ethyl-4-phenylthiazol-2(3H)-yliene)thiophene-2-carboxamide is referred to as compound 5i.

N-(3-Methyl-4-phenylthiazol-2(3H)-yliene)benzamide is referred to as compound 5j.

N-(4-(2,4-Dimethylphenyl)-3-methylthiazol-2(3H)-yliene)-benzamide is referred to as compound 5k.

N-(4-(2,4-Dimethylphenyl)-3-ethylthiazol-2(3H)-ylidene) benzamide is referred to as compound 5l.

N-(4-(2,4-Dimethylphenyl)-3-propylthiazol-2(3H)-ylidene) benzamide is referred to as compound 5m.

N-(3-Butyl-4-(2,4-dimethylphenyl)thiazol-2(3H)-ylidene) benzamide is referred to as compound 5n.

N-(4-(2,4-Dimethylphenyl)-3-hexylthiazol-2(3H)-ylidene)benzamide is referred to as compound 5o.

N-(4-(2,4-Dimethylphenyl)-3-dodecylthiazol-2(3H)-ylidene)benzamide is referred to as compound 5p.

N-(3-Allyl-4-(2,4-dimethylphenyl)thiazol-2(3H)-ylidene)benzamide is referred to as compound 5q.

N-(4-(2,4-Dimethylphenyl)-3-(prop-2-yn-1-yl)thiazol-2(3H)-ylidene)benzamide is referred to as compound 5r.

N-(4-(2,4-Dimethylphenyl)thiazol-2-yl)-N-(prop-2-yn-1-yl)benzamide is referred to as compound 6.

N-Ethyl-N-(4-phenylthiazol-2-yl)benzamide is referred to as compound 7a.

N-(4-Phenyl-3-propylthiazol-2(3H)-ylidene)benzamide is referred to as compound 7b.

N-(3-Allyl-4-phenylthiazol-2(3H)-ylidene)benzamide is referred to as compound 7c.

N-(4-Phenyl-3-(prop-2-yn-1-yl)thiazol-2(3H)-ylidene)benzamide is referred to as compound 7d.

N-(4-phenyl-3-ethylthiazol-2(3H)-ylidene)benzamide is referred to as compound 8a.

N-(4-Phenylthiazol-2-yl)-N-propylbenzamide is referred to as compound 8b.

N-(4-(2,4-Dimethylphenyl)thiazol-2-yl)benzenesulfonamide is referred to as compound 10.

N-(4-(2,4-Dimethylphenyl)-3-methylthiazol-2(3H)-ylidene)benzenesulfonamide is referred to as compound 11.

N-(4-(2,4-Dimethylphenyl)thiazol-2-yl)-N-methylbenzenesulfonamide is referred to as compound 12.

N-(4-Methylthiazol-2-yl)benzamide is referred to as compound 14a.

N-(4-(2-Chlorophenyl)thiazol-2-yl)benzamide is referred to as compound 14b.

N-(4-(3-Bromophenyl)thiazol-2-yl)benzamide is referred to as compound 14c.

N-(4-(4-Bromophenyl)thiazol-2-yl)benzamide is referred to as compound 14d.

N-(4-(3-Chlorophenyl)thiazol-2-yl)benzamide is referred to as compound 14e.

N-(4-(3,5-Bis(trifluoromethyl)phenyl)thiazol-2-yl)benzamide is referred to as compound 14f.

N-(4-(3,4,5-Trimethoxyphenyl)thiazol-2-yl)benzamide is referred to as compound 14g.

N-(5-Methyl-4-phenylthiazol-2-yl)benzamide is referred to as compound 14h.

N-(4-(4-Fluorophenyl)-5-methylthiazol-2-yl)benzamide is referred to as compound 14i.

N-(5-(p-Tolyl)thiazol-2-yl)benzamide is referred to as compound 14j.

4-Methoxy-N-(4-(3,4,5-trimethoxyphenyl)thiazol-2-yl)benzamide is referred to as compound 14k.

4-Chloro-N-(4-(3,4,5-trimethoxyphenyl)thiazol-2-yl)benzamide is referred to as compound 14l.

3,4-Dimethoxy-N-(4-(3,4,5-trimethoxyphenyl)thiazol-2-yl)benzamide is referred to as compound 14m.

2,4-Dimethoxy-N-(4-(3,4,5-trimethoxyphenyl)thiazol-2-yl)benzamide is referred to as compound 14n.

3,4,5-Trimethoxy-N-(4-(3,4,5-trimethoxyphenyl)thiazol-2-yl)benzamide is referred to as compound 14o.

2,3-Dimethoxy-N-(4-(3,4,5-trimethoxyphenyl)thiazol-2-yl)benzamide is referred to as compound 14p.

2-Methoxy-N-(4-(3,4,5-trimethoxyphenyl)thiazol-2-yl)benzamide is referred to as compound 14q.

3-Methoxy-N-(4-(3,4,5-trimethoxyphenyl)thiazol-2-yl)benzamide is referred to as compound 14r.

N-(3,4-Dimethylthiazol-2(3H)-ylidene)benzamide is referred to as compound 15a.

N-(4-(2-Chlorophenyl)-3-methylthiazol-2(3H)-ylidene)benzamide is referred to as compound 15b.

N-(4-(3-Bromophenyl)-3-methylthiazol-2(3H)-ylidene)benzamide is referred to as compound 15c.

N-(4-(4-Bromophenyl)-3-methylthiazol-2(3H)-ylidene)benzamide is referred to as compound 15d.

N-(4-(3-Chlorophenyl)-3-methylthiazol-2(3H)-ylidene)benzamide is referred to as compound 15e.

N-(4-(3,5-Bis(trifluoromethyl)phenyl)-3-methylthiazol-2(3H)-ylidene)benzamide is referred to as compound 15f.

N-(4-(3,4,5-Trimethoxyphenyl)-3-methylthiazol-2(3H)-yliene)-benzamide is referred to as compound 15g.

N-(3,5-Dimethyl-4-phenylthiazol-2(3H)-ylidene)benzamide is referred to as compound 15h.

N-(4-(4-Fluorophenyl)-3,5-dimethylthiazol-2(3H)-ylidene)benzamide is referred to as compound 15i.

N-(3-Methyl-5-(p-toyl)thiazol-2(3H)-ylidene)benzamide is referred to as compound 15j.

4-Methoxy-N-(3-methyl-4-(3,4,5-trimethoxyphenyl)thiazol-2(3H)-ylidene)benzamide is referred to as compound 15k.

4-Chloro-N-(3-methyl-4-(3,4,5-trimethoxyphenyl)thiazol-2(3H)-ylidene)benzamide is referred to as compound 15l.

3-Methoxy-N-(3-methyl-4-(3,4,5-trimethoxyphenyl)thiazol-2(3H)-ylidene)benzamide is referred to as compound 15m.

N-(4-Cyclopropyl-3-methylthiazol-2(3H)-ylidene)benzamide is referred to as compound 15n.

3,4,5-Trimethoxy-N-(3-methyl-4-(3,4,5-trimethoxyphenyl)thiazol-2(3H)-ylidene) benzamide is referred to as compound 15o.

N-(4-(2-Chlorophenyl)thiazol-2-yl)-N-methylbenzamide is referred to as compound 16a.

N-(4-(3-Bromophenyl)thiazol-2-yl)-N-methylbenzamide is referred to as compound 16b.

N-(4-(4-Bromophenyl)thiazol-2-yl)-N-methylbenzamide is referred to as compound 16c.

N-Methyl-N-(4-(3,4,5-trimethoxyphenyl)thiazol-2-yl)benzamide is referred to as compound 16d.

N-(4-(4-Fluorophenyl)-5-methylthiazol-2-yl)-N-methylbenzamide is referred to as compound 16e.

N-Methyl-N-(5-(p-tolyl)thiazol-2-yl)benzamide is referred to as compound 16f.

4-Methoxy-N-methyl-N-(4-(3,4,5-trimethoxyphenyl)thiazol-2-yl)benzamide is referred to as compound 16g.

3,4-Dimethoxy-N-methyl-N-(4-(3,4,5-trimethoxyphenyl)thiazol-2-yl)benzamide is referred to as compound 16h.

2,4-Dimethoxy-N-methyl-N-(4-(3,4,5-trimethoxyphenyl)thiazol-2-yl)benzamide is referred to as compound 16i.

3,4,5-Trimethoxy-N-methyl-N-(4-(3,4,5-trimethoxyphenyl)thiazol-2-yl)benzamide is referred to as compound 16j.

2,3-Dimethoxy-N-methyl-N-(4-(3,4,5-trimethoxyphenyl)thiazol-2-yl)benzamide is referred to as compound 16k.

2-Methoxy-N-methyl-N-(4-(3,4,5-trimethoxyphenyl)thiazol-2-yl)benzamide is referred to as compound 16l.

3-Methoxy-N-methyl-N-(4-(3,4,5-trimethoxyphenyl)thiazol-2-yl)benzamide is referred to as compound 16m.

Compounds 2a-16m are referred to collectively as thiazole derived, anti-migration and anti-invasion agents, thiazole analogs, or thiazole derived compounds, throughout the disclosure. The chemical structures of compounds 2a-16m are provided below.

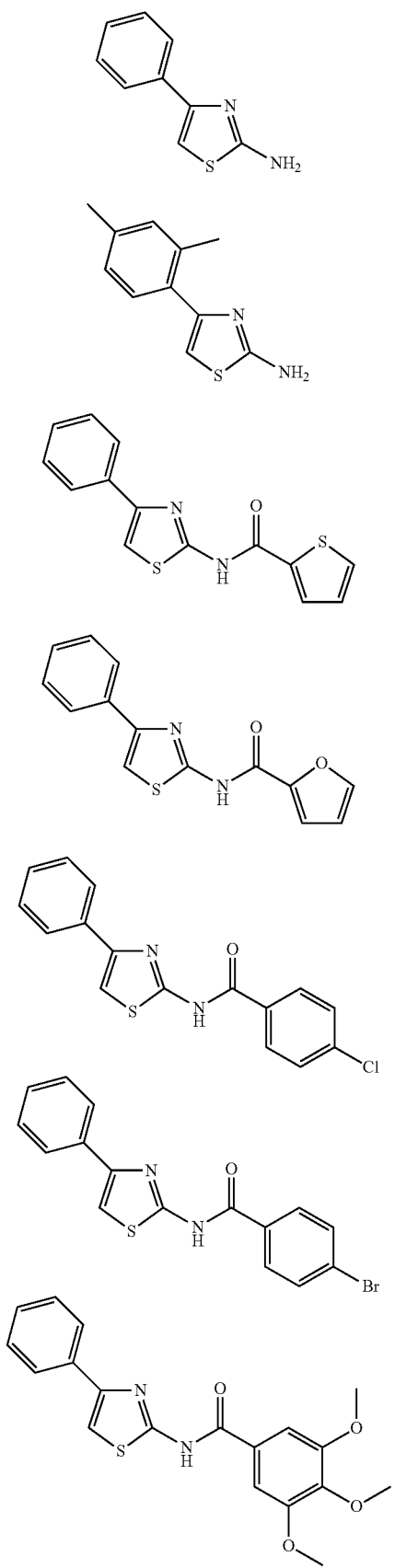
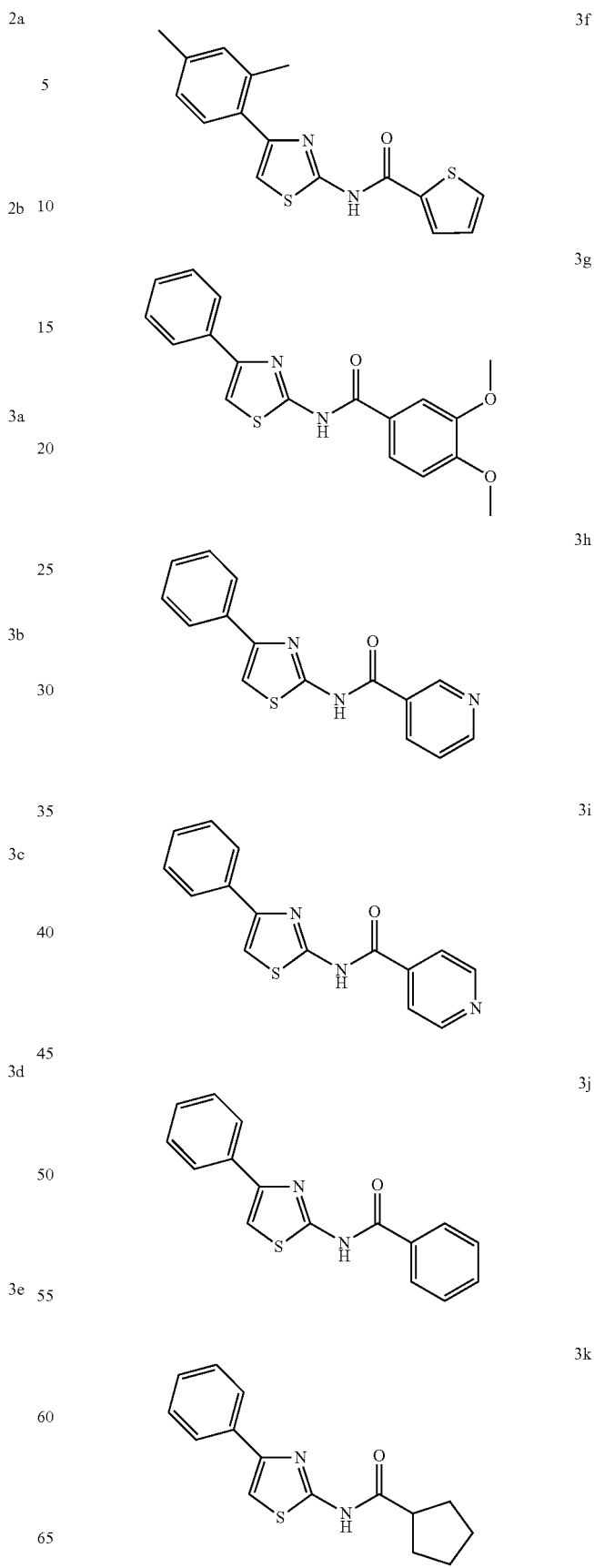

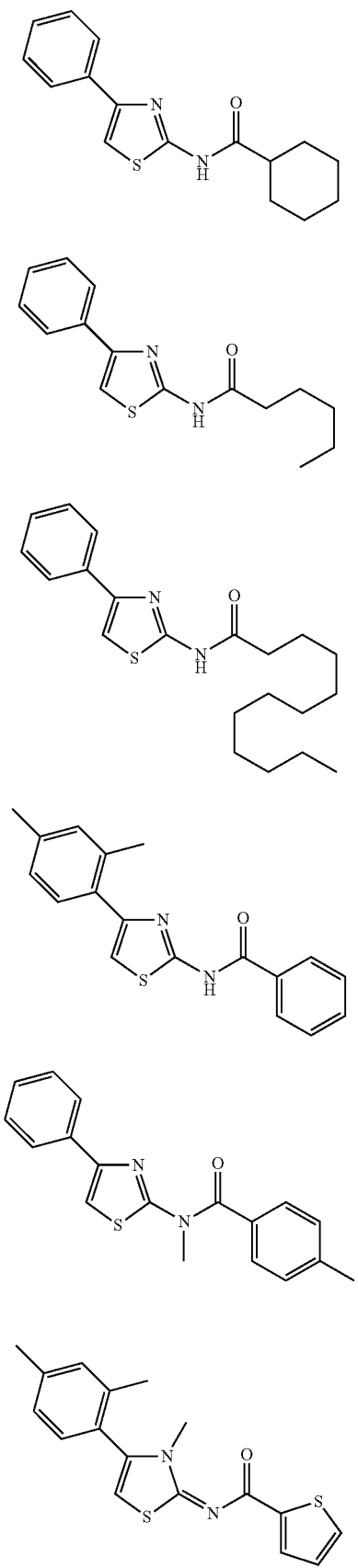

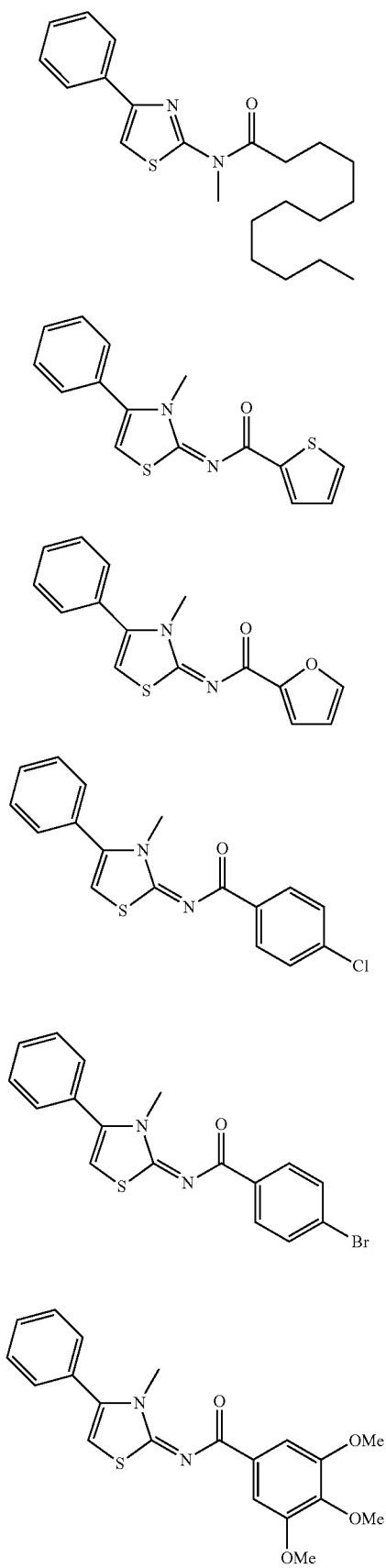
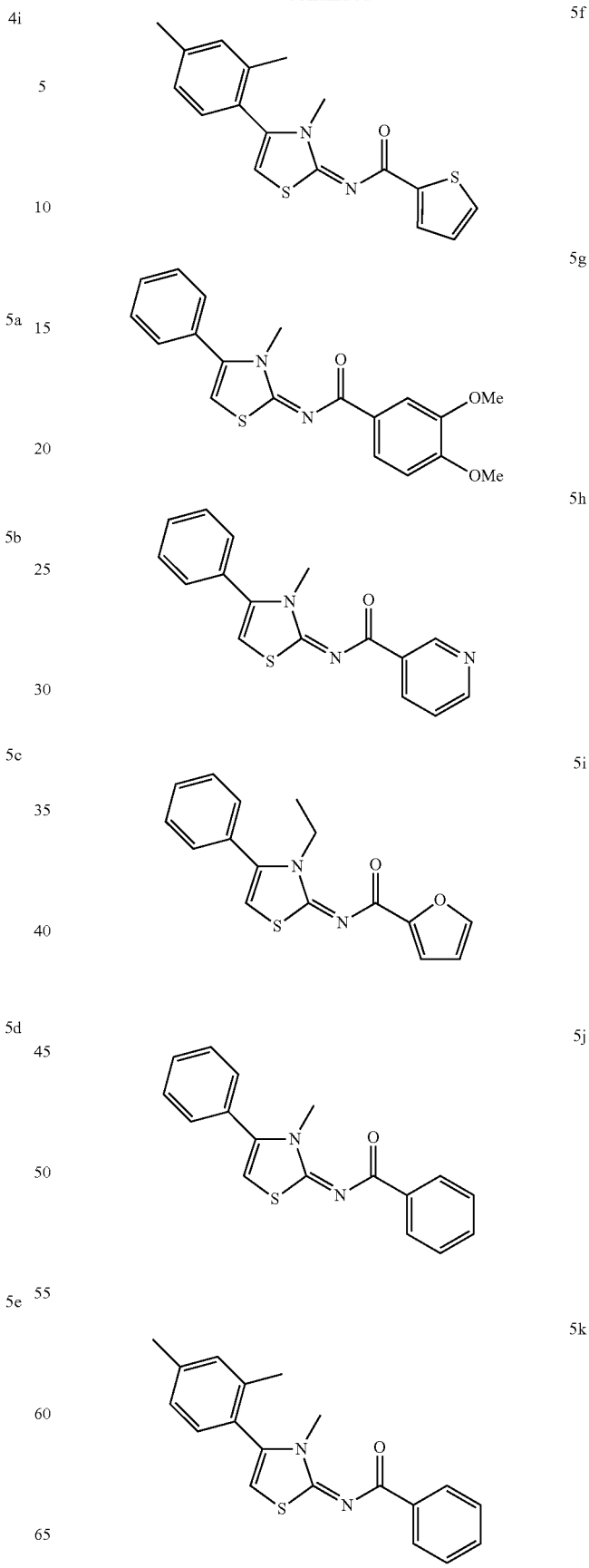

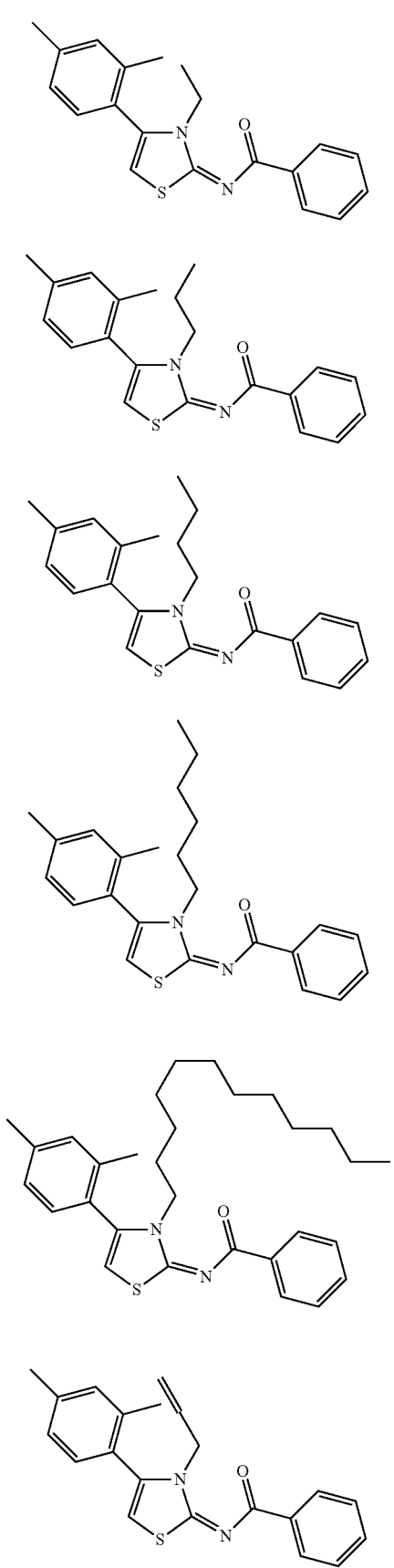
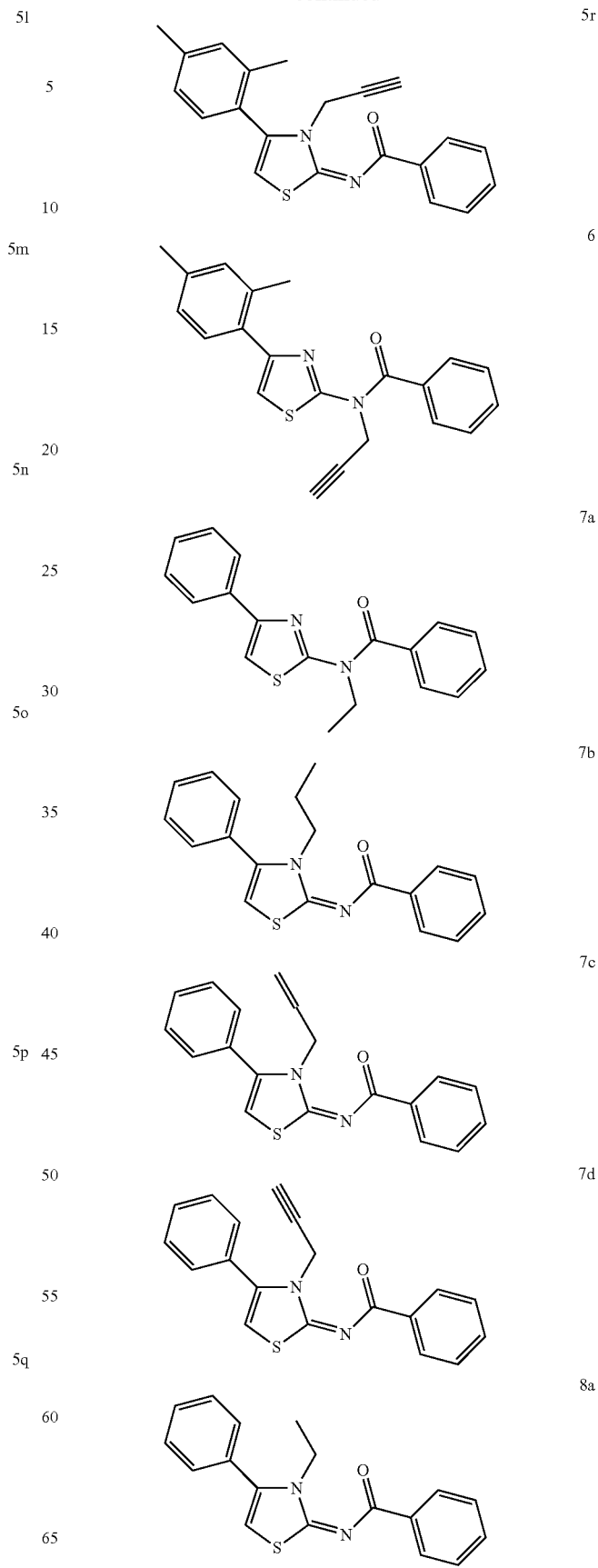

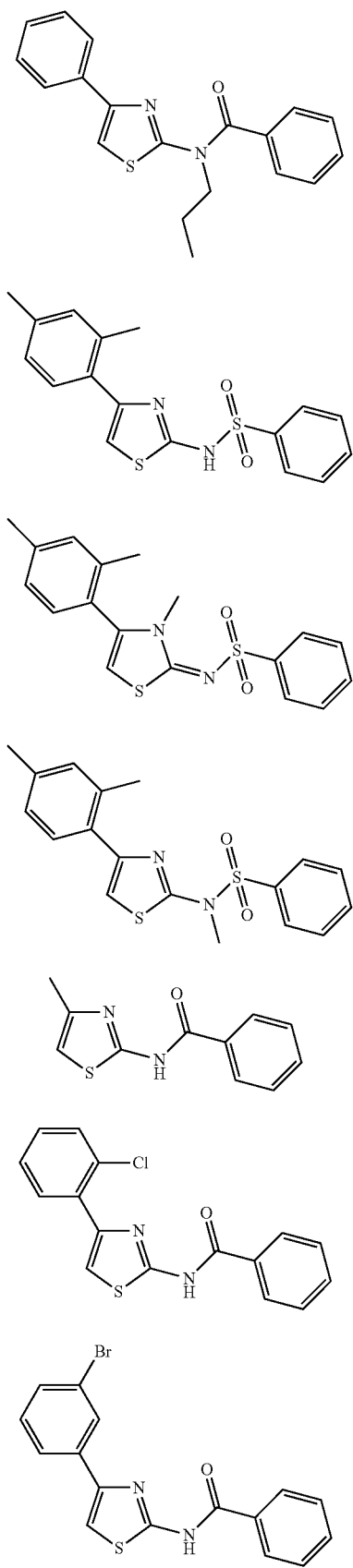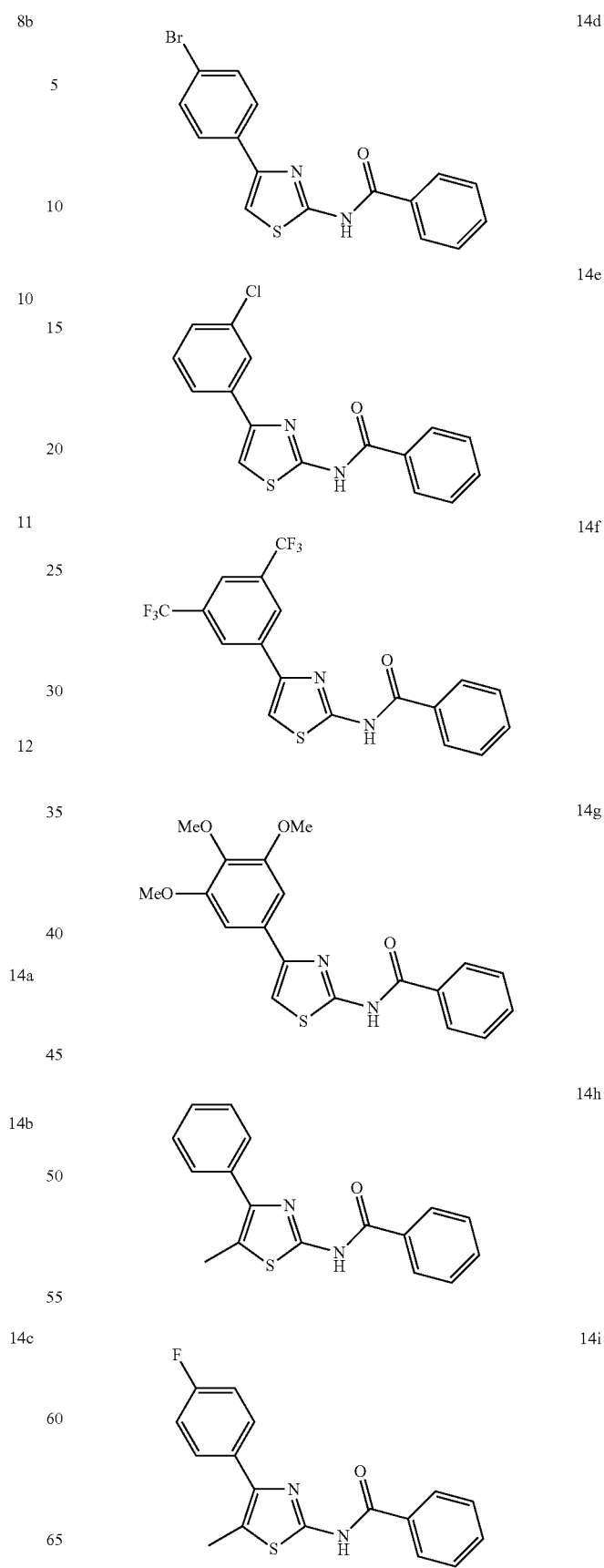

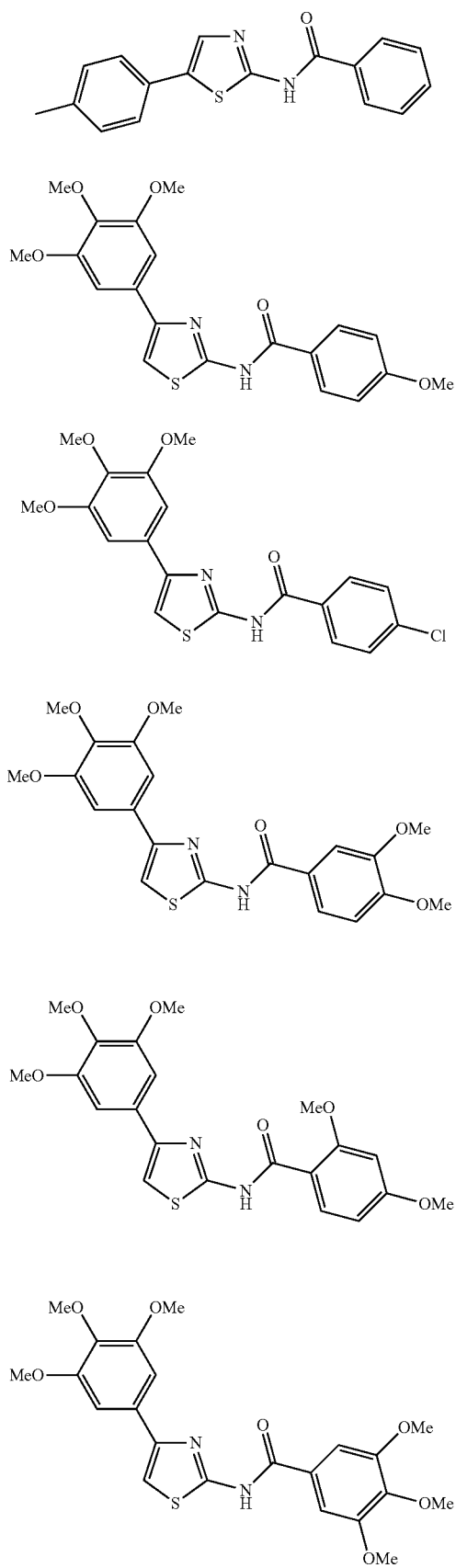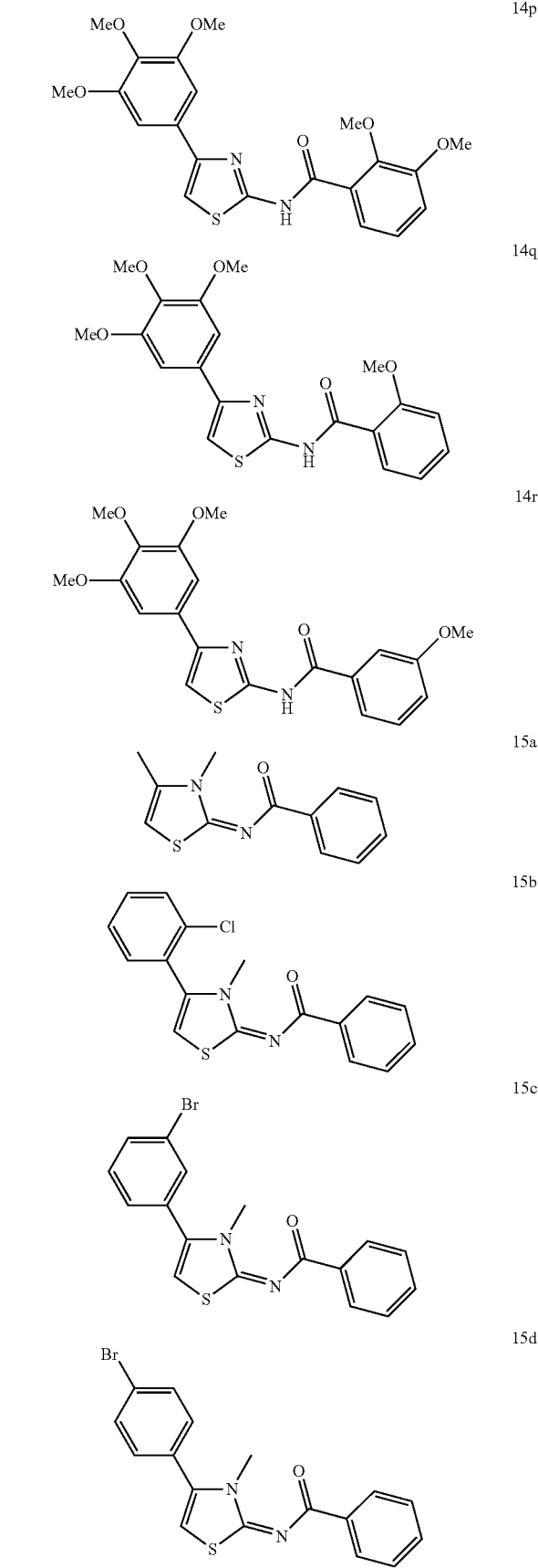

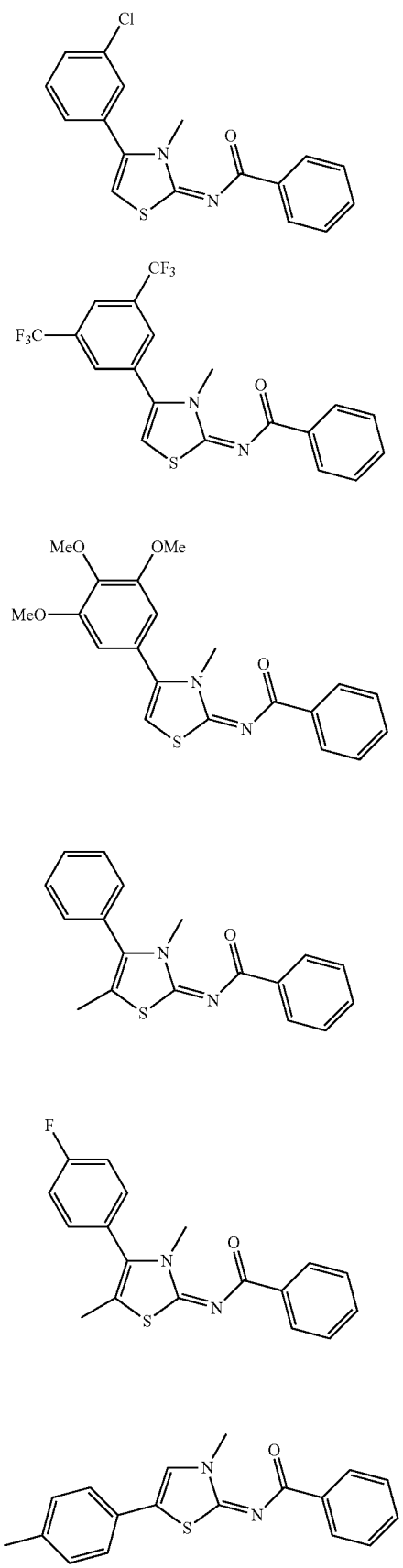
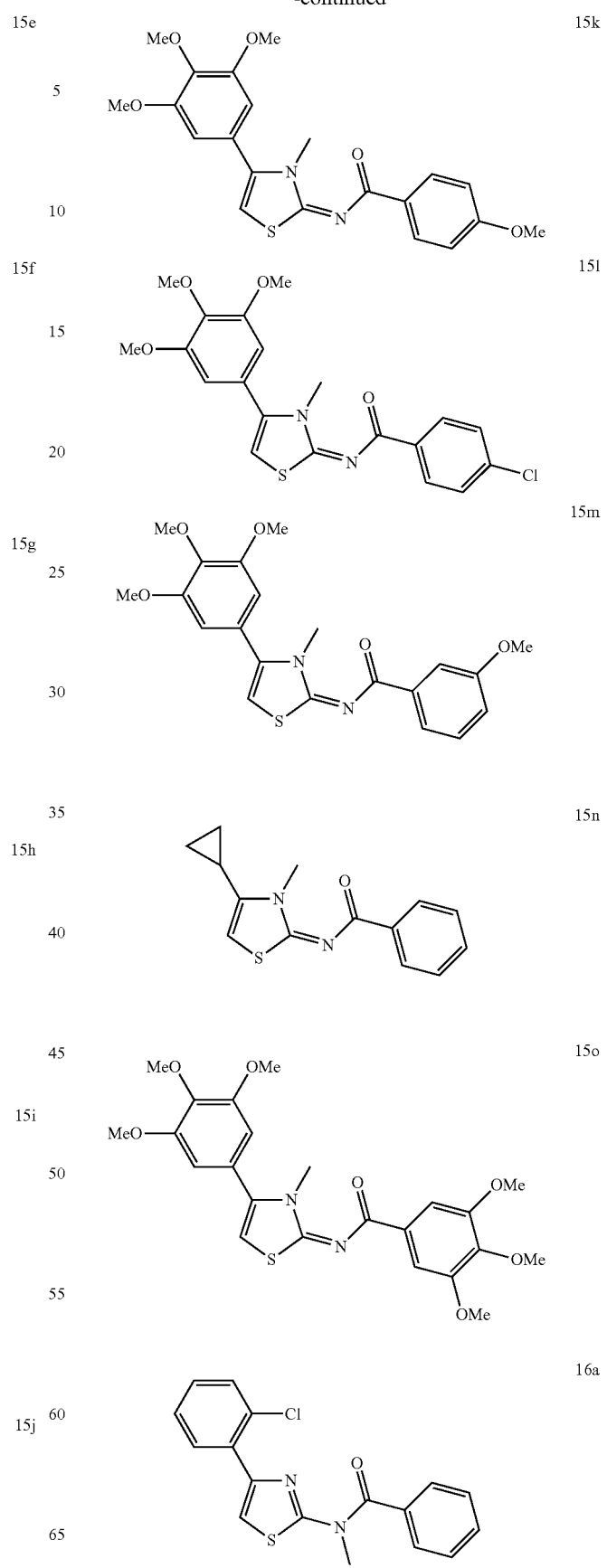

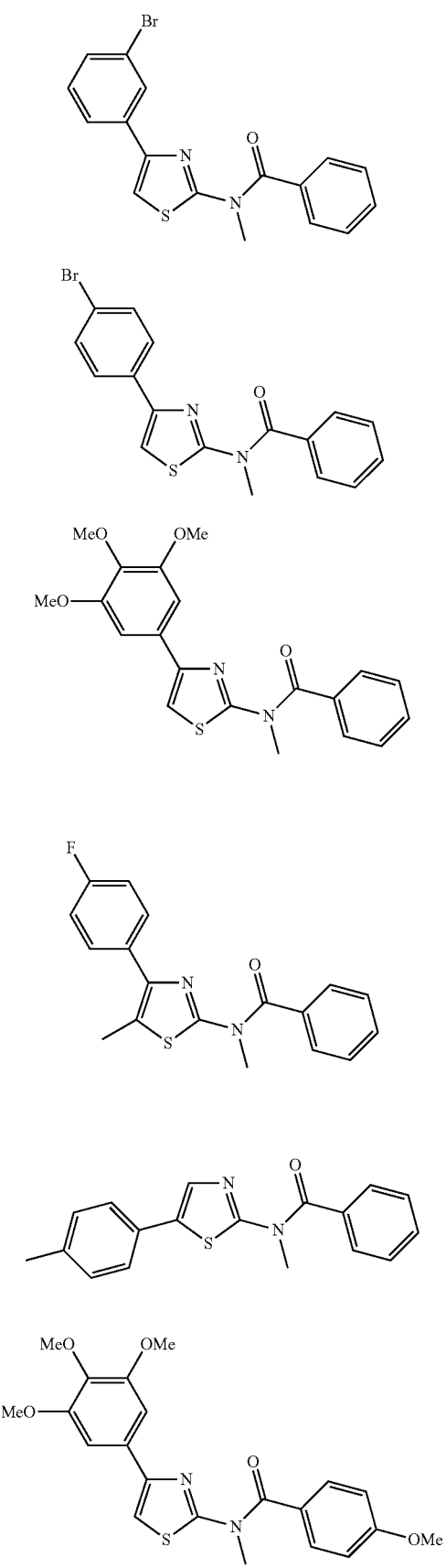
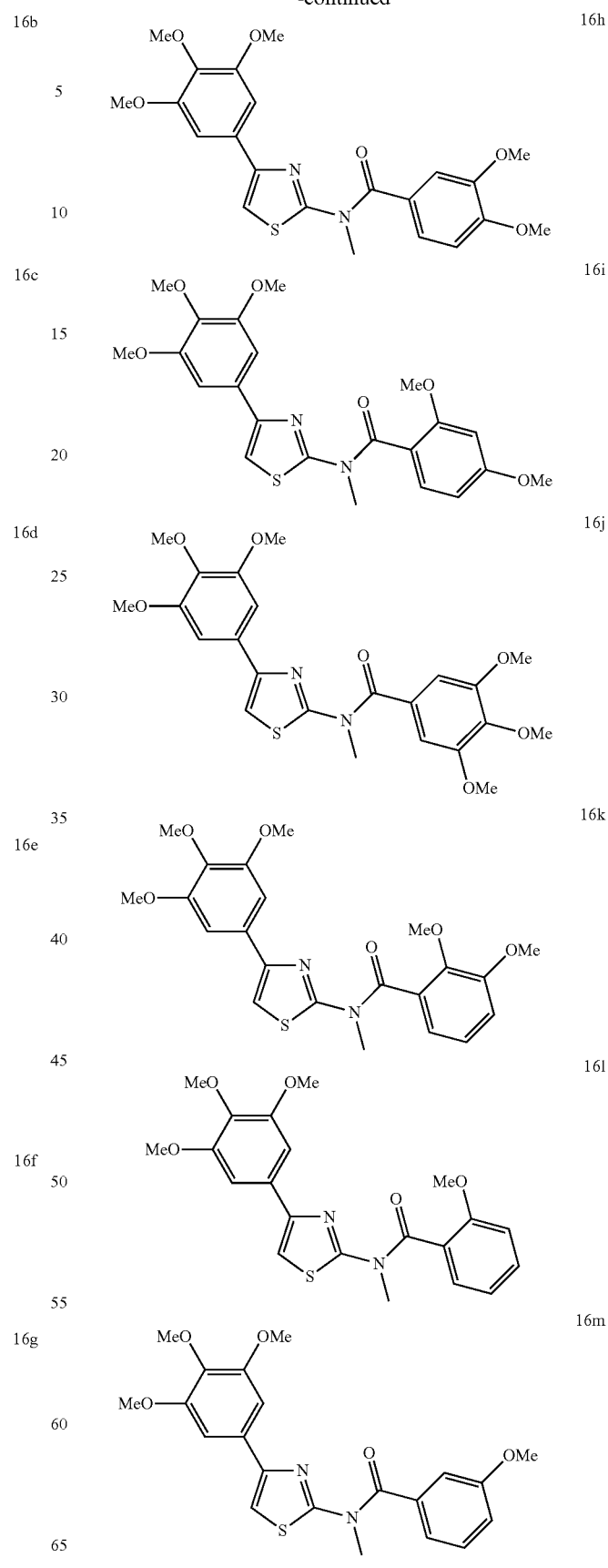

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated, and in its operation, may be made without departing in any way from the spirit of the present invention. No feature of the invention is critical or essential unless it is expressly stated as being critical or essential.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

One aspect of the present invention describes the synthesis of novel thiazole analogs. Another embodiment of the invention describes the potent anti-migration and anti-invasion effects on metastatic cancer cells exhibited by the disclosed thiazole analogs.

Figure 3:
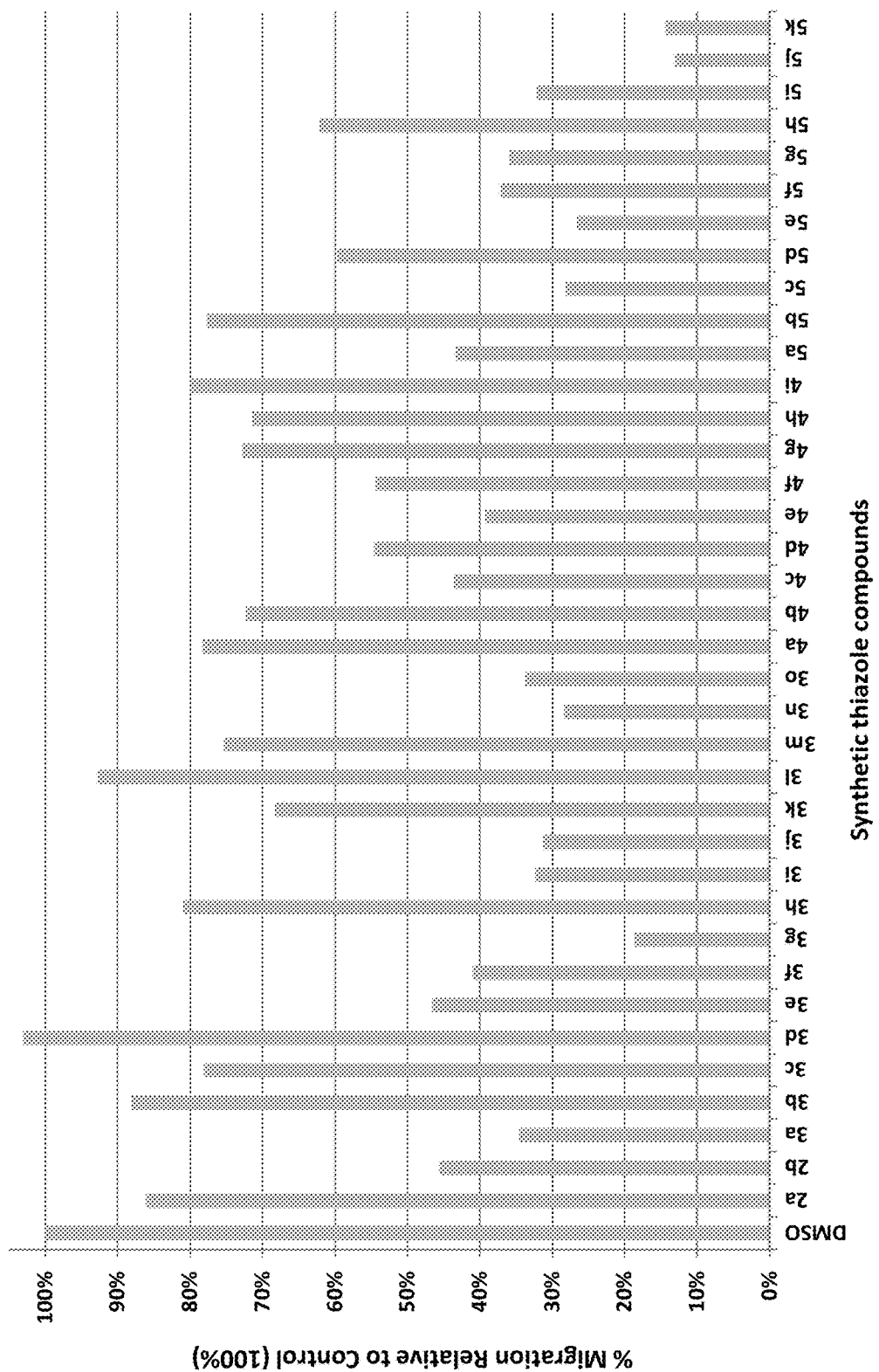
FIG. 3 shows that the thiazole analogs inhibit migration of MDA-MB-231 breast cancer cells.
Figure 4:
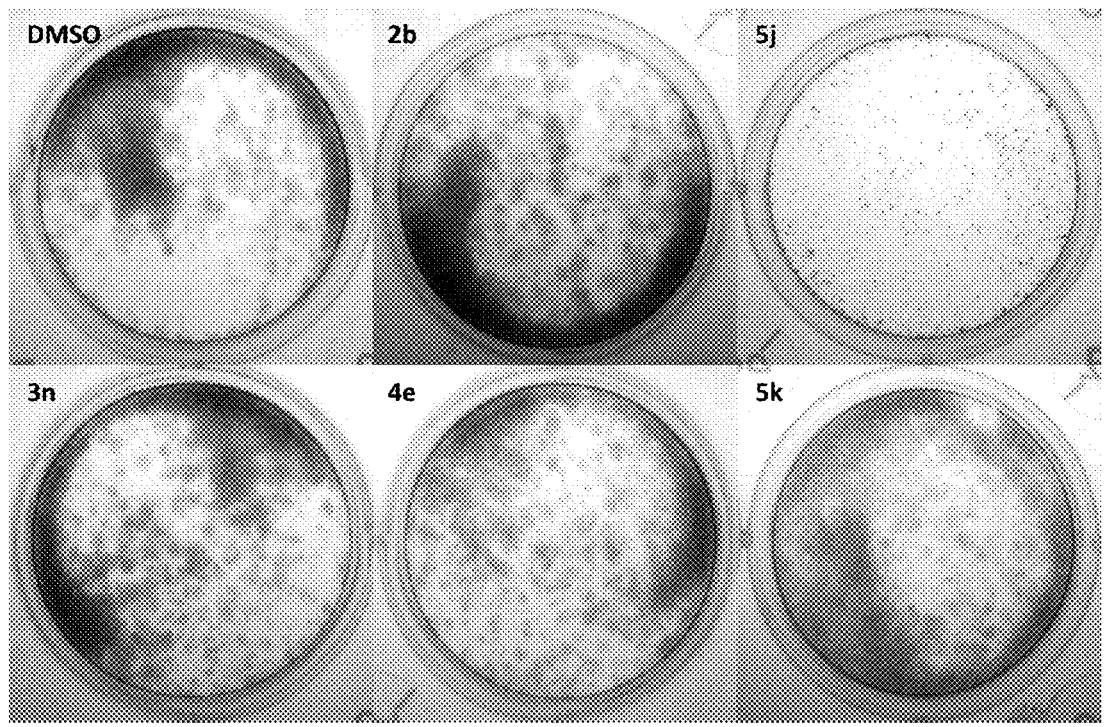
FIG. 4 shows clonogenic assay results demonstrating no cytotoxicity of the thiazole analogs that potently inhibit migration of MDA-MB-231 cells in four out of five selected compounds. Images of colony formation are shown for cells treated with 1) DMSO, 2) 2b, 3) 5j, 4) 3n, 5) 4e, and 6) 5k.
Figure 5:
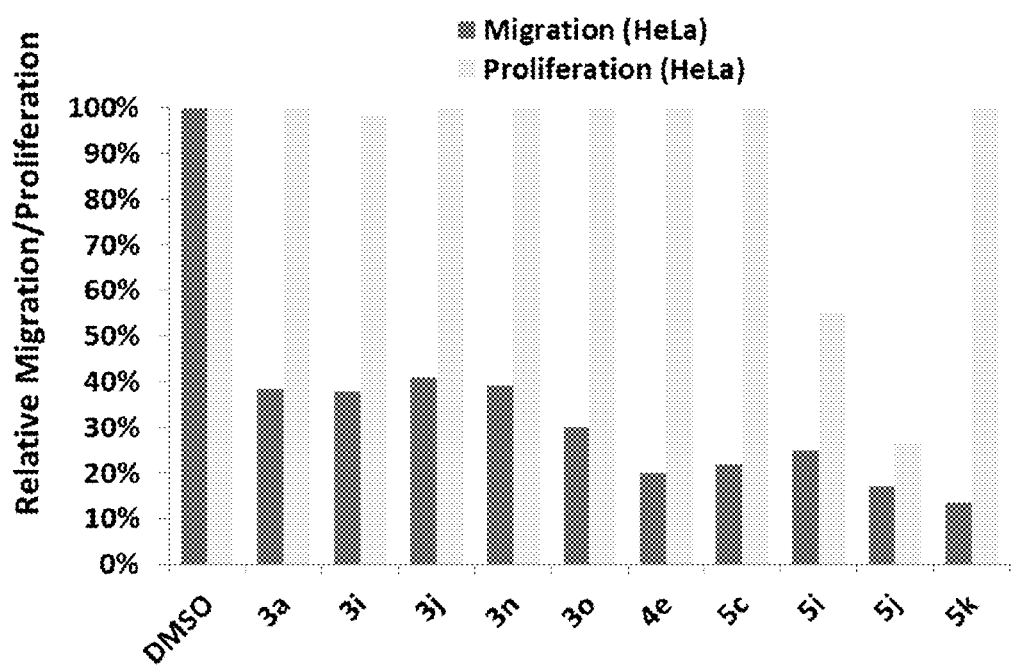
FIG. 5 shows the effect of selected thiazole analogs on the migration and proliferation of HeLa cells.
Figure 6:
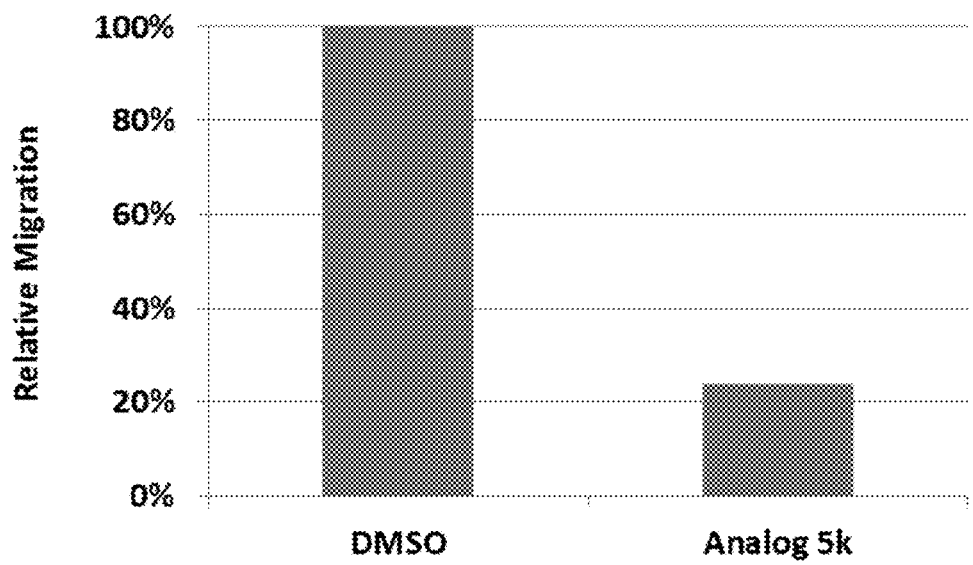
FIG. 6 shows that analog 5k strongly inhibits migration of A549, a metastatic non-small cell lung cancer cell line.

To determine if these analogs have anti-migration and anti-invasion activities in different cancer cell lines, transwell migration assays were performed using MDA-MB-231 breast cancer cells (FIG. 3) and HeLa cells (FIG. 5) for all synthetic analogs. The most potent analog, 5k, was also tested in a non-small cell lung cancer cell line, A549 (FIG. 6). Next, clonogenic assays were performed on the breast cancer cells treated with the compounds to rule out any indirect effect on cell migration due to cytotoxicity (FIG. 4). MDA-MB-231 cells were allowed to grow for 14 days in six-well plates in the presence or absence of the synthetic compounds at 10 µM.

As used herein, the term "metastatic cancer" refers to any cancer having invasive and metastatic potential. The terms "minimize" or "reduce," or derivatives thereof, include a complete or partial inhibition of a specified biological effect (which is apparent to one of ordinary skill from the context in which the terms "minimize" or "reduce" are used).

Methods of Administration

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example: calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the invention generally include any amount sufficient to: (1) detectably limit actin polymerization in a cell of interest; (2) detectably inhibit cancer presentations, such as metastasis; or (3) alleviate symptoms of cancer in a patient or animal treated with a thiazole analog described herein.

The amount of thiazole analog active ingredient that may be combined with the carrier materials to produce a single dosage form will vary depending upon the host treated and the particular mode of administration. It will be understood, however, that the specific dose level for any particular patient will depend upon a variety of factors including the activity of the specific thiazole analog employed, the age, body weight, general health, sex, diet, time of administration, route of administration, rate of excretion, drug combination, and the severity of the particular disease being treated.

Accordingly, the novel thiazole analogs of the present invention can be provided in vivo to a mammal in need thereof, in any manner, for treatment of metastatic cancer for example, with the desired outcome of blocking or delaying the onset of metastasis. The thiazole analogs of the present invention can be provided by any route acceptable for administration, and at any dose acceptable for a non-cytotoxic therapeutic agent.

For example, the thiazole analogs of the present invention can be provided to an animal at about 0.01, about 0.1, about 1, about 5, about 10, about 20, about 30, or about 40 mg per kilogram per animal per day. The thiazole analogs of the present invention can be provided at from about 0.01 to about 40, from about 0.1 to about 40, from about 1 to about 40, from about 5 to about 40, from about 10 to about 40, from about 20 to about 40, from about 30 to about 40, from about 0.01 to about 30, from about 0.01 to about 20, from about 0.01 to about 10, from about 0.01 to about 5, and from about 0.01 to about 1 mg per kilogram per day. A particular embodiment of the present invention comprises administration of the thiazole compound 5k at at least one of the aforementioned dosages.

As aforementioned, the thiazole analogs of the present invention can be administered at from about 1 mg to about 40 mg/kg of body weight daily, in a human or animal, being so treated. Further, a therapeutically effective dosage of a thiazole compound or composition comprising such a compound, may include a total daily dose administration of for example, from about 0.001 to 1000 mg/kg of body weight daily, or from about 0.01 to 100 mg/kg of body weight daily, or from about 0.1 to 10 mg/kg of body weight daily. Dosage unit compositions may contain such amounts of submultiples thereof to make up the daily dosages.

The thiazole compounds of the present invention may be administered orally, parenterally, sublingually, by aerosolization or inhalation of a spray, rectally, or topically, in dosage unit formulations containing conventional nontoxic pharmaceutically acceptable carriers, adjuvants, and vehicles as desired. Topical administration may also involve the use of transdermal administration such as transdermal patches.

Injectable preparations, for example, sterile injectable aqueous or oleaginous suspensions may be formulated according to the known art using skiable dispersing or wetting agents and suspending agents.

Solid dosage forms for oral administration may include capsules, tablets, pills, powders, and granules. In such solid dosage forms, the active thiazole analog may be admixed with at least one inert diluent such as sucrose, lactose, or starch. Such dosage forms may also comprise, as is normal practice, additional substances other than inert diluents.

While various preferred embodiments of the invention have been disclosed above, it will be appreciated that changes can be made to these embodiments without departing from the spirit and scope of the invention.

EXAMPLE 1

Synthesis of Thiazole Analogs

Figure 1A:
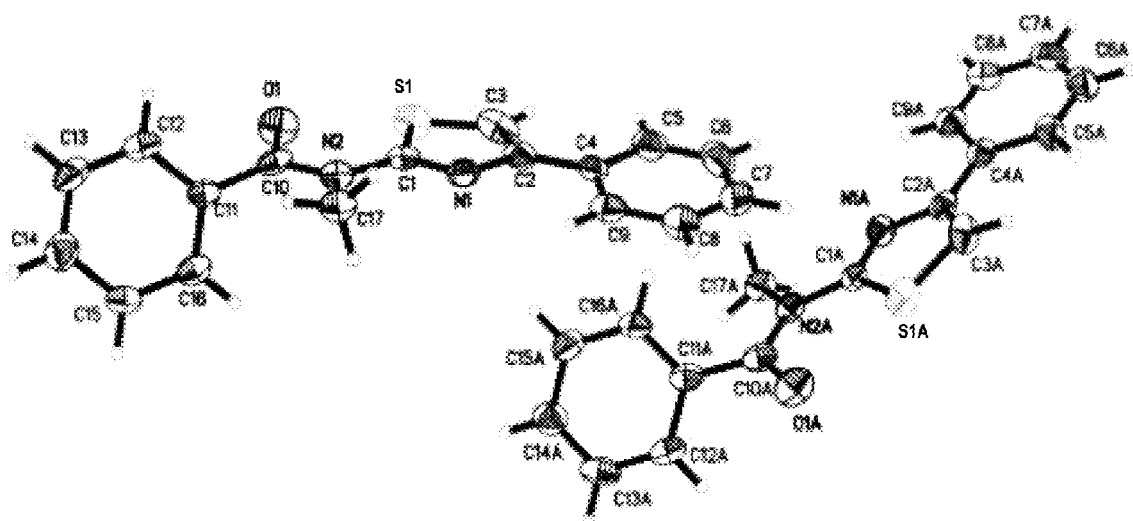
FIG. 1 shows the X-ray crystal structures of 4e (FIG. 1A) and 5j (FIG. 1B).
Figure 1B:
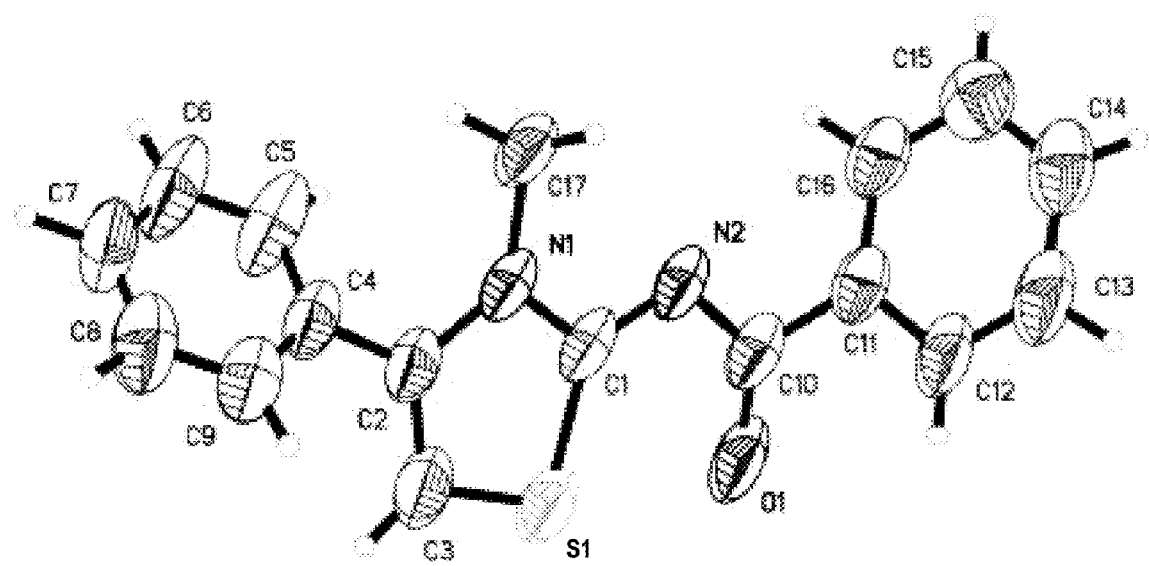
Figure 2:
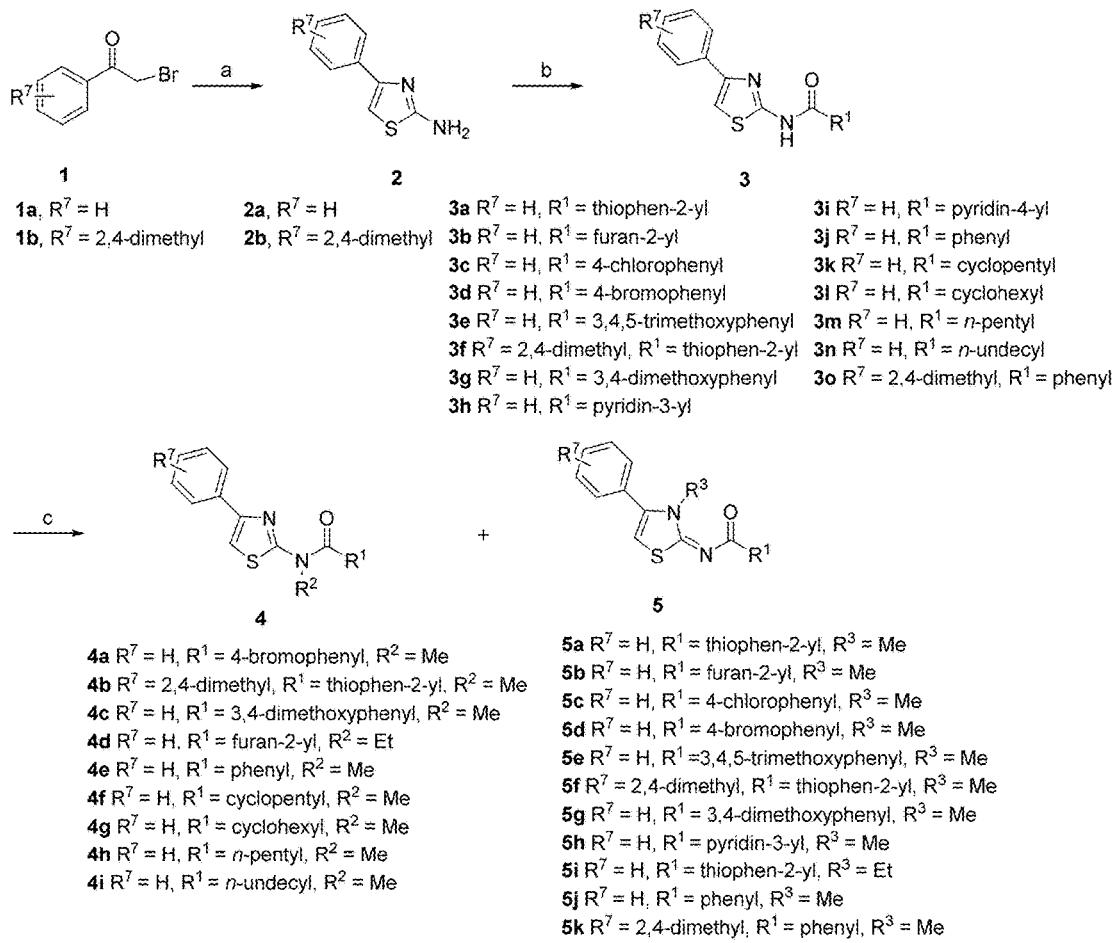
FIG. 2 shows the synthesis of novel anti-migration and anti-invasion thiazole analogs.

Thiazole derivatives were designed by varying the substituent groups $R^6$, $R^1$, $R^2$, and $R^3$ either individually or in combination on the basic structures of 2, 3, 4, and 5 as illustrated in FIG. 2.

To synthesize 2-Amino-4-phenylthiazole (2a), a mixture of 2-bromo-1-phenylethanone (19.9 g, 0.1 mol) and thiourea (8.4 g, 0.11 mol) in anhydrous EtOH (200 mL) was heated at reflux for 1 h. After that, the solvent was removed in vacuo, and saturated aqueous $NaHCO_3$ was added to make the mixture basic (pH=8-9). Then, the mixture was extracted with $CH_2Cl_2$. The combined organic phases were washed with brine and dried with $MgSO_4$. After removal of the solvent, the residue was stirred for 20 min with petroleum ether and filtered to afford 2a (17.1 g, 97%) as a solid. H-NMR (CDCl$_3$): 7.78-7.76 (2H, m), 7.40-7.36 (2H, m), 7.31-7.27 (1H, m), 6.72 (1H, s), 5.13 (2H, s, br). MS-EI: 176 (M$^+$). HRMS (ESI(+)): Calcd. for $C_9H_9N_2S$ (M+H): 177.0486. Found: 177.0477.

To synthesize 2-Amino-4-(2,4-dimethylphenyl)thiazole (2b), a mixture of 2-bromo-1-(2,4-dimethyl phenyl)ethanone (22.7 g, 0.1 mol) and thiourea (8.4 g, 0.11 mol) in anhydrous EtOH (200 mL) was heated at reflux for 1 h. After that, the solvent was removed in vacuo, and saturated aqueous $NaHCO_3$ was added to make the mixture basic (pH=8-9). Then, the mixture was extracted with $CH_2Cl_2$. The combined organic phases were washed with brine and dried with $MgSO_4$. After removal of the solvent, the residue was stirred for 20 min with petroleum ether and filtered to afford 2b (24.6 g, 100%) as a solid. $^1$H-NMR (CD$_3$OD): 7.27 (1H, J=7.6 Hz, d), 7.19 (1H, s), 7.13 (1H, J=0.4 and 7.6 Hz, dd), 6.74 (1H, s), 2.35 (3H, s), 2.34 (3H, s). MS-EI: 204 (M$^+$). HRMS (ESI(+)): Calcd. for $C_{13}H_{13}N_2S$ (M+H): 205.0799. Found: 205.0798.

To synthesize analogs 3a, 3b, 3c, 3d, 3e, and 3f, a solution of 2 (0.01 mol) and $R^1CO_2H$ (0.015 mol) was prepared in anhydrous dichloromethane, to which were added dicyclohexylcarbodimide (0.02 mol) and DMAP (0.61 g, 0.005 mol). After stirring overnight at room temperature under nitrogen atmosphere, petroleum ether was added to the reaction mixture to facilitate precipitates, and then the solution was filtered, and concentrated in vacuo. The residue was purified by flash chromatography to give the corresponding 3 analogs as solid.

To synthesize analogs 3g, 3h, 3i, 3j, 3k, 3l, 3m, 3n, and 3o, a mixture of $R^1CO_2H$ (0.015 mol) and thionyl chloride (7.12 g, 4.4 mL, 0.06 mol) was refluxed for 2 h followed by removal of excess thionyl chloride in vacuo. To a solution of 2 (0.01 mol) and DMAP (1.24 g, 0.01 mol) in anhydrous dichloromethane was added the above acyl chloride or commercially available acyl chloride in dichloromethane dropwise at 0° C. After stirring at room temperature for 2 h under nitrogen atmosphere, the reaction mixture was concentrated in vacuo. The saturated $Na_2CO_3$ solution was added to quench the reaction, and the solution was extracted with ethyl acetate, dried over $MgSO_4$, and concentrated in vacuo. The residue was purified by flash chromatography to give the desired 3 analogs as a solid.

To synthesize analogs 4 and 5, a cooled mixture of NaH (0.26 g, 60% in oil, 6.5 mmol) in THF (20 mL) was prepared, to which was added a solution of various 3 analogs (5 mmol) in THF (10 mL) dropwise. The mixture was warmed up to room temperature and stirred for 20 min. After that, the mixture was cooled to 0° C. again and MeI or EtBr (6.5 mmol) was added dropwise. The mixture was then warmed up to room temperature and stirred for 2 h. Water (5 mL) was added to quench the reaction and the mixture was further diluted with water (50 mL). The mixture was extracted with $CH_2Cl_2$ (3×50 mL). The combined organic phase was dried with anhydrous $MgSO_4$. After removal of all the solvent, the residue was purified by silica gel chromatography (hexane/EtOAc=4:1) to afford product 4 and 5 (more polar) as solid.

EXAMPLE 2

Thiazole Analogs Inhibit Migration of MDA-MB-231 Breast Cancer Cells

To determine the effects of the synthesized mackroketone analogs on cancer cell migration, we performed transwell migration assay on each compound using an invasive and metastatic breast cancer cell line, MDA-MB-231. When cells were seeded at a density of $2.5 \times 10^4$ in media free of serum in the upper chamber but containing 5% FBS in the lower chamber, their ability to migrate in the presence and absence of 10 μM analogs were measured by counting the total number of cells in the lower chamber after 24 hrs. As shown in FIG. 3, of the 37 synthetic analogs, most displayed moderate or potent anti-migration activity, 19 analogs showed greater than 50% inhibition, and three most potent analogs (3g, 5j and 5k) blocked cell migration by over 80%. These results demonstrate that the synthetic analogs are effective migration inhibitors.

EXAMPLE 3

Clonogenic Assay of MDA-MB-231 Cells Treated with Analogs

To rule out any indirect effect on cell migration due to cytotoxicity, clonogenic assays were performed on the breast cancer cells treated with the compounds. MDA-MB-231 cells were allowed to grow for 14 days in six-well plates in the presence or absence of the synthetic compounds at 10 μM. FIG. 4 shows the proliferation and colony formation of five anti-migration analog-treated colony images compared to DMSO treated control cells. The five compounds, 2b, 5j, 3n, 4e, and 5k all inhibited cell migration by over 50% (55% to 86%), yet no apparent cell toxicity was observed when cells were treated with the analogs at the same dose of 10 μM for two weeks, with the exception of 5j, which significantly inhibited colony formation of the breast cancer cells by 75%. A few other anti-migration analogs also exhibit moderate level of inhibition of the breast cancer cell proliferation. For example, analog 3g blocked both cell migration (81.4%) and colony formation (42.7%). For these analogs cytotoxicity may have partially contributed to their overall anti-migration effect. The cell toxicity data for all analogs are listed in Table 1 along with anti-migration data for comparison.

TABLE 1

List of all synthetic analogs with migration inhibition and colony formation data when MDA-MB-231 breast cancer cells were treated with 10 μM analogs

| Analogs | Migration Inhibition (% of vehicle control) | Effect on cell proliferation (colony formation) (% of vehicle control) |
|---|---|---|
| DMSO | 100.0% | 100.0% |
| 2a | 86.0% | 103.6% |
| 2b | 45.5% | 110.9% |
| 3a | 34.5% | 85.9% |
| 3b | 88.0% | 98.8% |
| 3c | 78.0% | 95.0% |
| 3d | 103.0% | 98.6% |
| 3e | 46.5% | 80.9% |
| 3f | 40.9% | 67.5% |
| 3g | 18.6% | 57.3% |
| 3h | 80.8% | 102.8% |
| 3i | 32.3% | 95.5% |
| 3j | 31.3% | 105.2% |
| 3k | 68.2% | 99.8% |
| 3l | 92.7% | 103.4% |
| 3m | 75.2% | 90.7% |
| 3n | 28.3% | 71.5% |
| 3o | 33.7% | 85.0% |
| 4a | 78.2% | 107.7% |
| 4b | 72.2% | 97.7% |
| 4c | 43.5% | 97.1% |
| 4d | 54.5% | 96.5% |
| 4e | 39.2% | 123.4% |
| 4f | 54.3% | 132.4% |
| 4g | 72.7% | 97.5% |
| 4h | 71.4% | 127.5% |
| 4i | 80.0% | 111.1% |
| 5a | 43.3% | 85.0% |
| 5b | 77.6% | 107.3% |
| 5c | 28.1% | 98.2% |
| 5d | 59.7% | 63.8% |
| 5e | 26.5% | 75.4% |
| 5f | 37.1% | 102.3% |
| 5g | 35.9% | 40.9% |
| 5h | 62.0% | 111.5% |
| 5i | 32.1% | 97.7% |
| 5j | 13.0% | 25.2% |
| 5k | 14.3% | 120.9% |

EXAMPLE 4

Anti-Migration Activities and Effect on Colony Formation in Metastatic HeLa Cells Based on the potent effects of synthetic thiazole analogs in blocking migration of MDA-MB-231 cells, ten analogs with high anti-migration activity but low or negligible cytotoxicity were selected to test their anti-migration activity in another metastatic cell line, HeLa. For comparison of possible cancer cell specific mode of action we also included 5j, a potent anti-migration analog that also inhibited the proliferation of the triple negative breast cancer cells. Results are summarized in FIG. 4. The analogs exhibited excellent anti-migration activity in HeLa cells, as evidenced by the dramatically reduced transwell migration (60-86% inhibition) when treated with 10 μM analogs. While these analogs demonstrated similar anti-migration efficacies in MDA-MB-231 and HeLa cells, some differences were noted. For example, the analog 3n showed 30% inhibition of colony formation in MDA-MB-231 cells but had no apparent cytotoxicity in HeLa cells. On the other hand, the analog 5i was not toxic to 231 cells, but it suppressed the clonogenic capability of HeLa cells by 45%. Interestingly, the analog 5j was a strong inhibitor of cell proliferation for both HeLa and MDA-MB-231 cells. The analog that emerged as the most potent anti-migration agent with no apparent cytotoxicity in both metastatic breast cancer and cervical cancer cell lines was 5k, achieving over 85% inhibition of transwell migration in both cell lines at the dose of 10 μM. Thus 5k may be further evaluated for its potential as an anti-migration and anti-metastatic agent.

EXAMPLE 5

Antimigration Activity of Thiazole Analog 5k in A549 Non Small Cell Lung Cancer Cells Additional migration assay of a non small cell lung cancer cell line, A549 also demonstrated that in the presence of 10 µM 5k, the metastatic lung cancer cells lost nearly 80% of migratory capacity as indicated in FIG. 6.

EXAMPLE 6

Thiazole Analogs Show Low IC50 Concentration in MDA-MB-231 Cells

Given the potent anti-migration efficacy demonstrated by most of the thiazole analogs, we decided to study the dose response of the most potent analogs to obtain their IC50 values in suppressing the transwell migration of the MDA-MB-231 cells. As shown in Table 2, the IC50 values for the 10 selected analogs varied from 2.87 µM to 0.176 µM.

TABLE 2

| $IC_{50}$ values for 10 most potent anti-migration compounds in MDA-MB-231 breast cancer cells | |
|---|---|
| Compound | $IC_{50}$ (µM) |
| 3a | 2.49 |
| 3i | 2.87 |
| 3j | 1.29 |
| 3n | 1.01 |
| 3o | 0.839 |
| 4e | 0.366 |
| 5c | 1.12 |
| 5i | 2.08 |
| 5j | 0.189 |
| 5k | 0.176 |

EXAMPLE 7

Effect of Selected Thiazole Analogs on the Invasion of MDA-MB-231 Breast Cancer Cells To determine if the synthetic thiazole analogs block invasion of metastatic cancer cells we performed matrigel invasion assays of MDA-MB-231 cells treated with 10 selected analogs.

Figure 7:
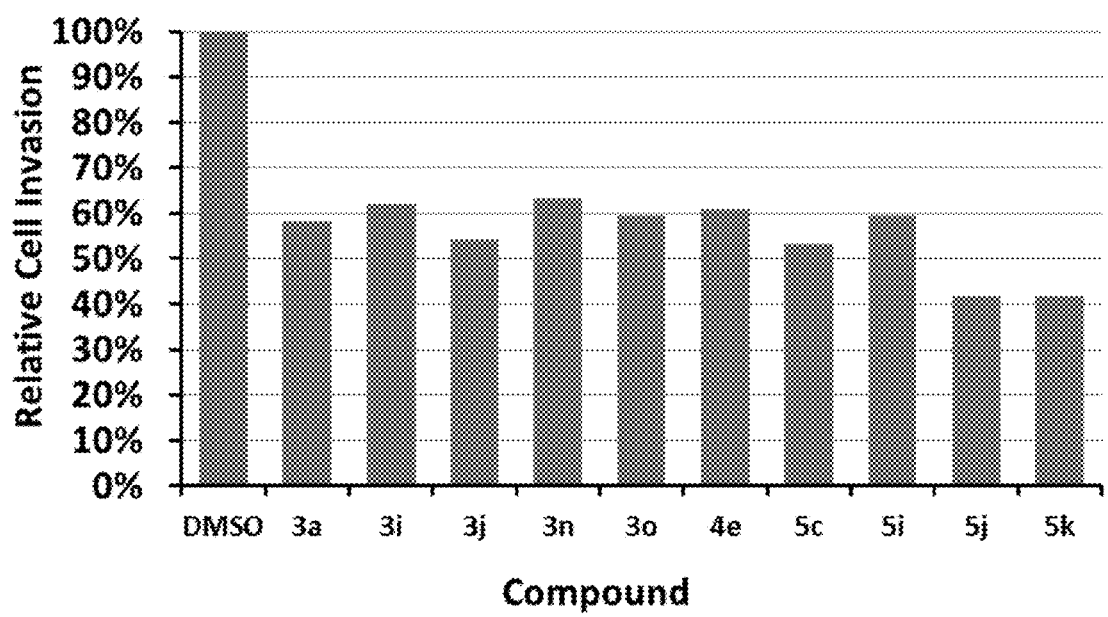
FIG. 7 shows the effect of selected thiazole analogs on the invasion of MDA-MB-231 breast cancer cells.

As shown in FIG. 7, all 10 analogs exhibited marked inhibition of matrigel invasion of the breast cancer cells, with percent invasion reduced to approximately 40-60% of the control.

The analog 5k, the most active anti-migration agent without any apparent cytotoxicity, also appears to be the most potent compound in blocking cell invasion.

EXAMPLE 8

Figure 8:
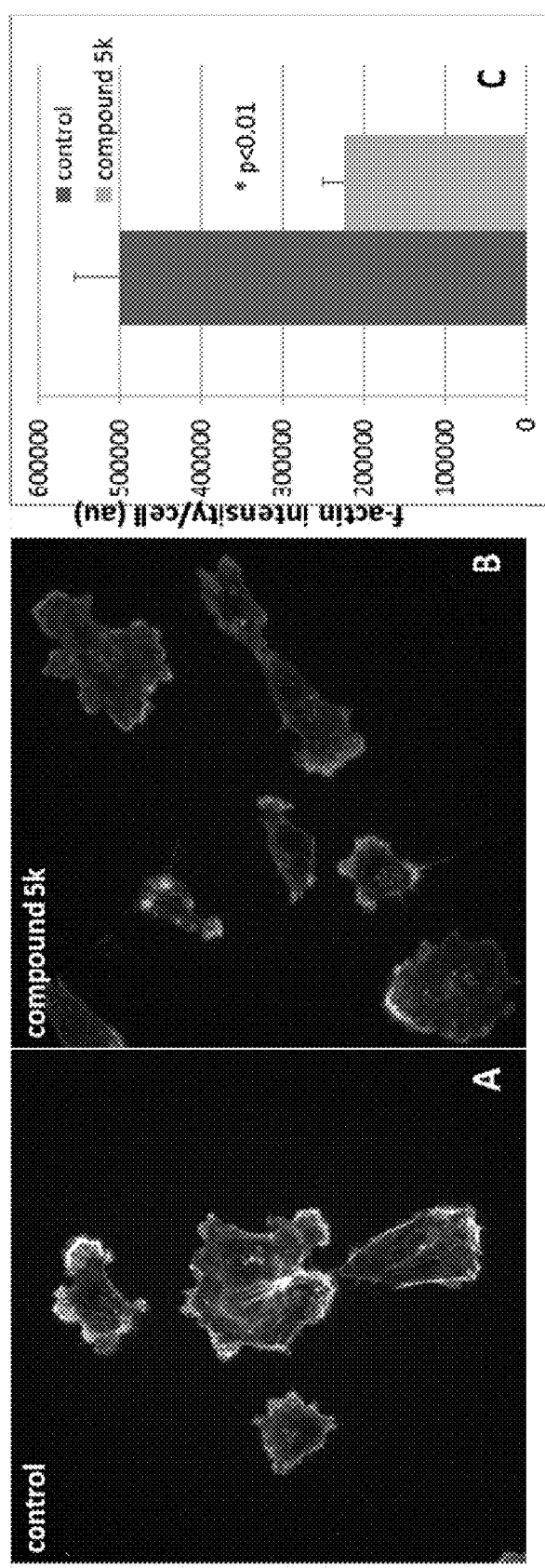
FIG. 8 shows the possible mechanism of action of 5k in blocking cell migration and invasion. Analog 5k strongly suppresses actin-rich membrane protrusions in MDA-MB-231 cells. F-actin staining in (A) Control cells (DMSO-treated); or (B) Cells treated with 5k; and (C). Quantitation of-actin intensity in vehicle and 5k-treated cells.

Analog 5k Strongly Suppresses Actin-Rich Membrane Protrusions in MDA-MB-231 Breast Cancer Cells An essential component of migration is protrusion of the cell membrane, which is driven by actin polymerization. The related compound known as migrastatin has been shown to block actin bundling by binding to the actin regulatory protein fascin, which is linked to migration in cell culture systems, and metastasis in vivo. See Chen, L.; Yang, S.; Jakoncic, J.; Zhang, J. J.; Huang, X. Y. Migrastatin analogues target fascin to block tumour metastasis. Nature 2010; 464:1062-1066. Erratum in: Nature. 2011; 476:240; Hashimoto, Y., D. J. Kim, and J. C. Adams. The roles of fascins in health and disease. J. Pathol. 2011; 224:289-300; and Jayo, A., and M. Parsons. Fascin: a key regulator of cytoskeletal dynamics. Int. J. Biochem. Cell Biol. 2010; 42:1614-1617. While the previous study by Chen et al. showed that migrastatin blocked the actin bundling activity of fascin using purified proteins in vitro, the effects on actin structures in cells were not tested. See Chen, 2010. Thus, we tested the hypothesis that compound 5k interferes with f-actin in membrane protrusions associated with cell motility. MDA-MB-231 cells were serum starved –/+10 µM 5k, then stimulated with serum for 2 hours to induce actin-rich membrane protrusions, which were analyzed by fluorescent microscopy. FIG. 8 shows that control cells (DMSO-treated) had robust actin-rich membrane protrusions, which were significantly reduced in cells treated with 5k (55% reduction in f-actin intensity; $p<0.01$).

EXAMPLE 9

Figure 9:
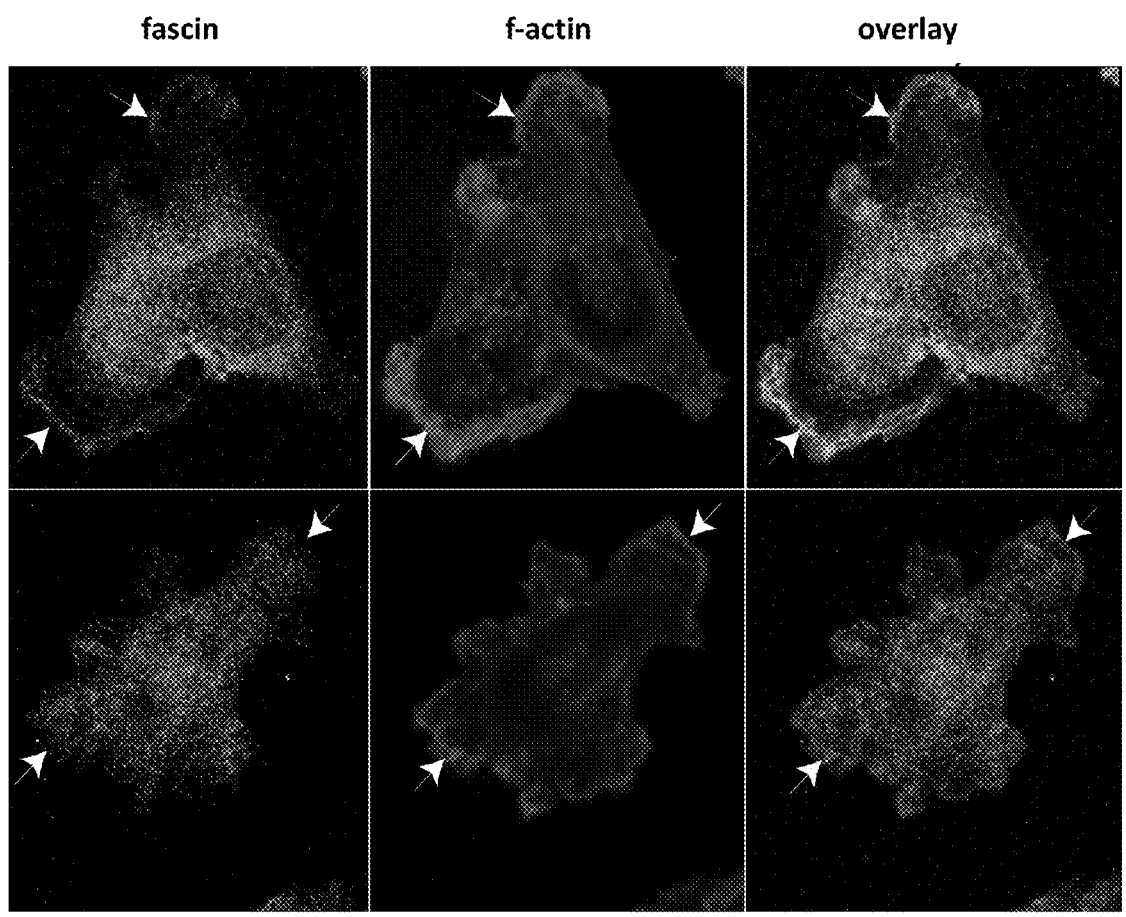
FIG. 9 shows the immunofluorescence microscopic images of localization of fascin (green) and f-actin (magenta) in MDA-MB-231 cells treated with DMSO (vehicle) or synthetic analog 5k. Co-localization of f-actin and fascin appears as white pixels.

Compound 5k Significantly Blocks f-Actin and is Correlated with the Absence of Fascin in Membrane Protrusions To further probe for a possible role of fascin in the reduction of actin-rich membrane protrusions, we determined the localization of fascin by immunofluorescence microscopy. FIG. 9 shows that in control cells, a pool of fascin is localized within the zone of f-actin in the protrusions. This pool of fascin was notably missing from the actin-rich membrane regions in the cells treated with 5k (indicated by arrowheads). Thus, the results demonstrate that compound 5k significantly blocks f-actin and is correlated with the absence of fascin in the membrane protrusions, suggesting that its mechanism of action is to perturb the actin dynamics required for tumor cell migration.

EXAMPLE 10

Synthesis of Additional Thiazole Analogues

Figure 10:
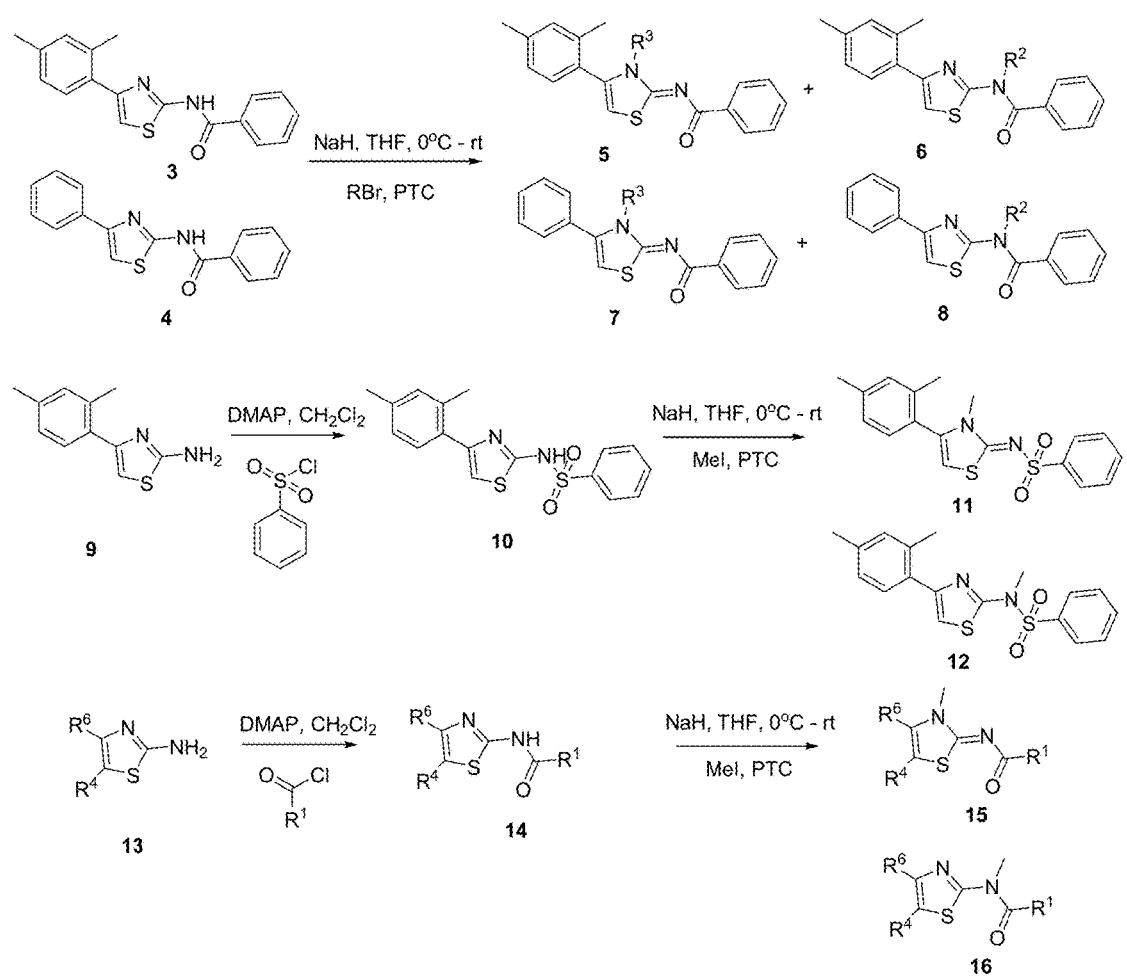
FIG. 10 shows a reaction scheme for synthesis of the analogs of lead compounds. NaH is sodium hydride; THF is tetrahydrofuran; "rt" is room temperature; RBr indicates a brominated R group that provides the $R^2$ and $R^3$ substituents of compounds 5-8, as shown; PTC is phase transfer catalyst; DMAP is 4-dimethylaminopyridine; and MeI is methyl iodide.

As shown in FIG. 10, the compounds 5, 7 and their isomers 6 and 8 were respectively obtained from N-alkylation of the amides 3 and 4 which were prepared following the literature procedure. See Zheng, S.; Zhong, Q.; Jiang, Q.; Mottamal, M.; Zhang, Q.; Zhu, N.; Burow, M. E.; Worthylake, R. A.; Wang, G. Discovery of a series of thiazole derivatives as novel inhibitors of metastatic cancer cell migration and invasion. ACS Med. Chem. Lett. 2013; 4:191-196. 4-(2,4-Dimethylphenyl)thiazol-2-amine (9) was treated with benzenesulfonic chloride to give 10, which was transferred to the analog 11 and its isomer 12 by the N-methylation reaction in THF. The acylation of the 2-aminothiazoles 13 by acyl chloride provided the amides 14 at room temperature in dichloromethane, and further methylation of 14 led to the desired analogs 15 and their corresponding isomers 16.

All reagents and solvents were purchased from AK Scientific, Sigma-Aldrich Chemical Co., Fisher Scientific, ACROS and Pharmco-AAPER and were used as received. Aldrich Chemical Co. (WI, USA) or Acros organics (NY, USA) and were used as received. All organic solvents (Pharmco-AAPER) used were of reagent grade quality and were used without further purification. NMR spectra were recorded on a Bruker Fourier-300 spectrometer (Bruker Inc., Billerica, Mass.) in ppm. Melting points were determined with a Mel-temp II point apparatus and are uncorrected. Crude synthetic products were purified by the following methods: chromatography on Silica Gel (60-100 mesh, Fisher Scientific) column. Analytical thin layer chromatography (TLC) was performed on 250μ fluorescent plates (Agela Tech., DE, USA) and visualized by using UV light. For all products, the purity was ascertained to be greater than 95% by the HPLC method using a Shimadzu (Columbia, Md.) 2010 HPLC-UV/MS system with a C-18 reverse phase column and by GC-MS analyses using an Agilent Technologies 5975C inert MSD mass spectrometer.

General procedure for N-alkylation of 3 and 4. To a cooled mixture of NaH (0.26 g, 60% in oil, 6.5 mmol) in THF (20 mL) was added a solution of compound 3 or 4 (5 mmol) in THF (10 mL) dropwise. The mixture was warmed up to room temperature and stirred for 20 min. After that, the mixture was cooled to 0° C. again and MeI or RBr (6.5 mmol) was added dropwise. The mixture was then warmed up to room temperature and stirred for 2 h. Water (5 mL) was added to quench the reaction and the mixture was further diluted with water (50 mL). The mixture was extracted with $CH_2Cl_2$ (3×50 mL). The combined organic phase was dried with anhydrous $MgSO_4$. After removal of all the solvent, the residue was purified by silica gel chromatography (hexane/EtOAc=4:1) to afford product 5 (more polar) and 6 or 7 (more polar) and 8 as solid.

5l: $^1$H-NMR (300 MHz, $CDCl_3$): 8.37 (dd, J=1.8 and 8.1 Hz, 2H), 7.49-7.42 (m, 3H), 7.18-7.10 (m, 3H), 6.45 (s, 1H), 4.35 (m, 1H), 3.82 (m, 1H), 1.24 (t, J=6.9 Hz, 3H). $^{13}$C-NMR (75 MHz, $CDCl_3$): 174.1, 167.8, 140.1, 137.82, 137.75, 137.2, 131.3, 131.2, 130.6, 129.2, 128.0, 127.2, 126.8, 106.8, 42.1, 21.3, 19.6, 13.8. GC-MS: 336 (M$^+$).

5m: $^1$H-NMR (300 MHz, $CDCl_3$): 8.36 (m, 2H), 7.52-7.42 (m, 3H), 7.17-7.09 (m, 3H), 6.45 (s, 1H), 4.28 (m, 1H), 3.71 (m, 1H), 2.41 (s, 3H), 2.13 (s, 3H), 1.70 (m, 2H), 0.81 (t, J=7.5 Hz, 3H). $^{13}$C-NMR (75 MHz, $CDCl_3$): 174.0, 168.1, 140.0, 138.2, 137.7, 137.2, 131.3, 131.2, 130.7, 129.2, 128.0, 127.3, 126.8, 106.8, 48.5, 21.8, 21.3, 19.6, 11.2. GC-MS: 350 (M$^+$).

5n: $^1$H-NMR (300 MHz, $CDCl_3$): 8.36 (m, 2H), 7.52-7.42 (m, 3H), 7.17-7.09 (m, 3H), 6.45 (s, 1H), 4.33 (m, 1H), 3.73 (m, 1H), 2.40 (s, 3H), 2.14 (s, 3H), 1.64 (m, 2H), 1.22 (m, 2H), 0.81 (t, J=7.5 Hz, 3H). $^{13}$C-NMR (75 MHz, $CDCl_3$): 174.1, 168.1, 140.1, 138.2, 137.7, 137.2, 131.3, 131.2, 130.7, 129.2, 128.0, 127.3, 126.8, 106.9, 46.7, 30.4, 21.3, 19.9, 19.6, 13.6. GC-MS: 364 (M$^+$).

5o: $^1$H-NMR (300 MHz, $CDCl_3$): 8.36 (dd, J=1.5 and 7.8 Hz, 2H), 7.52-7.42 (m, 3H), 7.17-7.09 (m, 3H), 6.45 (s, 1H), 4.33 (m, 1H), 3.72 (m, 1H), 2.41 (s, 3H), 2.14 (s, 3H), 1.61 (m, 2H), 1.23-1.17 (m, 6H), 0.81 (t, J=7.5 Hz, 3H). $^{13}$C-NMR (75 MHz, $CDCl_3$): 174.1, 168.0, 140.1, 138.1, 137.7, 137.2, 131.3, 131.2, 130.7, 129.2, 128.0, 127.3, 126.8, 106.9, 46.9, 31.1, 28.2, 26.2, 22.4, 21.3, 19.6, 13.9. GC-MS: 392 (M$^+$).

5p: $^1$H-NMR (300 MHz, $CDCl_3$): 8.35 (m, 2H), 7.49-7.26 (m, 3H), 7.17-7.09 (m, 3H), 6.44 (s, 1H), 4.32 (m, 1H), 3.73 (m, 1H), 2.40 (s, 3H), 2.13 (s, 3H), 1.59-1.50 (m, 4H), 1.28-1.17 (m, 16H), 0.88 (t, J=7.5 Hz, 3H). $^{13}$C-NMR (75 MHz, $CDCl_3$): 174.1, 168.1, 140.0, 138.1, 137.7, 137.3, 131.3, 131.2, 130.7, 129.2, 128.0, 127.3, 126.8, 106.9, 46.9, 32.8, 31.9, 29.7, 29.6, 29.5, 29.4, 29.3, 28.9, 28.2, 26.5, 25.8, 22.7, 21.3, 19.6, 14.1. MS (ESI): 477 (M+H).

5q: $^1$H-NMR (300 MHz, $CDCl_3$): 8.35 (m, 2H), 7.51-7.41 (m, 3H), 7.14-7.07 (m, 3H), 6.46 (s, 1H), 5.87 (m, 1H), 5.10 (dd, J=1.2 and 10.2 Hz, 1H), 4.98 (dd, J=1.2 and 17.1 Hz, 2H), 4.42 (m, 1H), 2.40 (s, 3H), 2.13 (s, 3H). $^{13}$C-NMR (75 MHz, $CDCl_3$): 174.2, 168.1, 140.1, 137.8, 137.1, 131.3, 131.1, 130.8, 129.2, 128.0, 127.0, 126.6, 118.4, 106.8, 49.1, 21.3, 19.7. GC-MS: 348 (M$^+$).

5r: $^1$H-NMR (300 MHz, $CDCl_3$): 8.40 (m, 2H), 7.52-7.42 (m, 3H), 7.23-7.11 (m, 3H), 6.47 (s, 1H), 4.80 (m, 2H), 2.40 (s, 3H), 2.21 (m, 1H), 2.19 (s, 3H). $^{13}$C-NMR (75 MHz, $CDCl_3$): 174.4, 168.1, 140.4, 138.1, 137.1, 136.9, 131.6, 131.4, 130.8, 129.4, 128.1, 126.9, 126.4, 106.9, 77.3, 72.4, 36.0, 21.4, 19.9. MS (ESI): 347 (M+H).

6: $^1$H-NMR (300 MHz, $CDCl_3$): 8.36 (dd, J=1.5 and 8.1 Hz, 2H), 7.52-7.43 (m, 4H), 7.20 (s, 1H), 7.18 (s, 2H), 4.75 (m, 2H), 2.42 (s, 3H), 2.22 (m, 1H), 2.21 (s, 3H). $^{13}$C-NMR (75 MHz, $CDCl_3$): 174.7, 167.3, 141.0, 138.5, 136.2, 135.9, 131.9, 131.6, 130.5, 129.5, 128.1, 127.3, 124.8, 98.0, 76.97, 72.7, 37.1, 21.5, 19.6. MS (ESI): 347 (M+H).

7a: $^1$H-NMR (300 MHz, $CDCl_3$): 7.92 (m, 2H), 7.55-7.48 (m, 5H), 7.42 (m, 2H), 7.34 (m, 1H), 7.25 (s, 1H), 4.27 (q, J=7.5 Hz, 2H), 1.38 (t, J=7.5 Hz, 3H). $^{13}$C-NMR (75 MHz, $CDCl_3$): 170.6, 159.0, 149.5, 135.2, 134.8, 130.4, 128.68, 128.65, 127.8, 126.7, 126.0, 109.2, 45.2, 14.1. GC-MS: 308 (M$^+$).

7b: $^1$H-NMR (300 MHz, $CDCl_3$): 8.36 (dd, J=1.2 and 7.5 Hz, 2H), 7.50-7.39 (m, 8H), 6.52 (s, 1H), 4.19 (q, J=7.5 Hz, 2H), 1.76 (m, 2H), 0.83 (t, J=7.5 Hz, 3H). $^{13}$C-NMR (75 MHz, $CDCl_3$): 174.1, 168.5, 139.3, 137.2, 131.3, 130.9, 129.6, 129.5, 129.2, 128.8, 128.7, 128.0, 126.0, 107.2, 48.8, 21.9, 11.1. GC-MS: 322 (M$^+$).

7c: $^1$H-NMR (300 MHz, $CDCl_3$): 8.35 (dd, J=1.8 and 6.3 Hz, 2H), 7.49-7.43 (m, 8H), 6.55 (s, 1H), 5.98 (m, 1H), 5.19 (d, J=10.2 Hz, 1H), 4.98 (d, J=17.4 Hz, 1H), 4.82 (d, J=5.1 Hz, 2H). $^{13}$C-NMR (75 MHz, $CDCl_3$): 174.3, 168.5, 139.3, 137.0, 131.9, 131.4, 130.6, 129.7, 129.6, 129.2, 128.7, 128.0, 118.0, 107.1, 49.6. GC-MS: 320 (M$^+$).

7d: $^1$H-NMR (300 MHz, $CDCl_3$): 8.40 (d, J=6.6 Hz, 2H), 7.57-7.44 (m, 8H), 6.56 (s, 1H), 4.92 (d, J=2.1 Hz, 2H). $^{13}$C-NMR (75 MHz, $CDCl_3$): 174.4, 168.5, 138.6, 136.8, 131.6, 130.1, 129.9, 129.44, 129.37, 129.0, 128.1, 77.8, 72.8, 36.9. LC-MS (ESI): 319 (M+H).

8a: $^1$H-NMR (300 MHz, $CDCl_3$): 8.37 (dd, J=1.5 and 7.5 Hz, 2H), 7.51-7.40 (m, 8H), 6.52 (s, 1H), 4.26 (q, J=6.9 Hz, 2H), 1.34 (t, J=6.9 Hz, 3H). $^{13}$C-NMR (75 MHz, $CDCl_3$): 174.2, 168.1, 139.1, 137.1, 130.9, 129.6, 129.4, 129.2, 128.9, 128.0, 107.2, 42.5, 14.0. GC-MS: 308 (M$^+$).

8b: $^1$H-NMR (300 MHz, $CDCl_3$): 7.91 (dd, J=1.5 and 6.9 Hz, 2H), 7.53-7.32 (m, 8H), 7.24 (s, 1H), 4.18 (q, J=7.5 Hz, 2H), 1.83 (m, 2H), 0.83 (t, J=7.5 Hz, 3H). $^{13}$C-NMR (75 MHz, $CDCl_3$): 170.8, 159.3, 149.5, 135.2, 134.8, 130.4, 128.68, 128.66, 128.5, 127.9, 127.0, 126.0, 109.2, 51.6, 21.9, 11.2. GC-MS: 322 (M$^+$).

Procedure for Preparation of 10. To a solution of 9 (0.61 g, 3.0 mmol) and pyridine (0.96 mL, 12 mmol) in anhydrous dichloromethane was added benzenesulfonic chloride (0.76 mL, 6 mmol) in dichloromethane dropwise at 0° C. After stirring at room temperature for 2 h under nitrogen atmosphere, the reaction mixture was concentrated in vacuo. The saturated $Na_2CO_3$ solution was added to quench the reaction, and the solution was extracted with ethyl acetate, dried over $MgSO_4$, and concentrated in vacuo. The residue was purified by flash chromatography to give product 10 (0.57 g, 55% yield) as a solid. $^1$H-NMR (300 MHz, $CDCl_3$): 9.85 (bs, 1H), 7.93 (d, J=7.8 Hz, 2H), 7.53-7.43 (m, 3H), 7.16 (d, J=7.8 Hz, 1H), 7.08-7.04 (m, 3H), 6.26 (s, 1H), 2.34 and 2.32 (ds, 6H). $^{13}$C-NMR (75 MHz, $CDCl_3$): 168.7, 141.9, 140.1, 136.3, 136.1, 132.2, 132.0, 128.9, 128.7, 127.2, 126.5, 125.7, 103.6, 21.2, 20.4. GC-MS: 344 (M$^+$).

Methylation of 10 to afford 11 and 12. To a cooled mixture of NaH (0.07 g, 60% in oil, 1.6 mmol) in THF (5 mL) was added a solution of compound 10 (0.34 g, 1 mmol) in THF (5 mL) dropwise. The mixture was warmed up to room temperature and stirred for 20 min. After that, the mixture was cooled to 0° C. again and MeI (0.25 mL, 4.0 mmol) was added dropwise. The mixture was then warmed up to room temperature and stirred for 2 h. Water (3 mL) was added to quench the reaction and the mixture was further diluted with water (10 mL). The mixture was extracted with $CH_2Cl_2$ (3×10 mL). The combined organic phase was dried with anhydrous $MgSO_4$. After removal of all the solvent, the residue was purified by silica gel chromatography (hexane/EtOAc=4:1) to afford product 11 (more polar) (0.27 g, 75% yield) and 12 (0.034 g, 9% yield) as solid.

11: $^1$H-NMR (300 MHz, $CDCl_3$): 8.05-8.02 (m, 2H), 7.58-7.43 (m, 3H), 7.12-7.01 (m, 3H), 6.27 (s, 1H), 3.19 (s, 3H), 2.36 (s, 3H), 2.11 (s, 3H). $^{13}$C-NMR (75 MHz, $CDCl_3$): 166.8, 142.3, 140.6, 139.1, 137.6, 131.9, 131.4, 130.5, 128.6, 127.1, 126.6, 126.4, 103.5, 33.6, 21.3, 19.5. GC-MS: 358 ($M^+$).

12: $^1$H-NMR (300 MHz, $CDCl_3$): 7.83 (d, J=7.2 Hz, 2H), 7.58-7.38 (m, 4H), 7.02-6.98 (m, 2H), 6.88 (s, 1H), 3.45 (s, 3H), 2.32 and 2.30 (ds, 6H). $^{13}$C-NMR (75 MHz, $CDCl_3$): 160.0, 151.2, 137.9, 136.8, 135.9, 133.8, 131.8, 131.4, 129.4, 129.3, 127.4, 126.6, 112.0, 36.7, 21.2, 21.1. GC-MS: 358 ($M^+$).

General Procedure for the Acylation of 13 (see FIG. 10) to afford 14 (see FIG. 10). To a solution of 13 (0.01 mol) and DMAP (1.24 g, 0.01 mol) in anhydrous dichloromethane was added the acyl chloride in dichloromethane dropwise at 0° C. After stirring at room temperature for 2 h under nitrogen atmosphere, the reaction mixture was concentrated in vacuo. The saturated $Na_2CO_3$ solution was added to quench the reaction, and the solution was extracted with ethyl acetate, dried over $MgSO_4$, and concentrated in vacuo. The residue was purified by flash chromatography to give product 14 as a solid.

14a: $^1$H-NMR (300 MHz, $CDCl_3$): 7.99 (dd, J=1.5 and 8.4 Hz, 2H), 7.52-7.47 (m, 3H), 6.55 (d, J=0.9 Hz, 1H), 2.11 (s, 3H). $^{13}$C-NMR (75 MHz, $CDCl_3$): 172.0, 165.3, 159.3, 146.8, 133.1, 132.8, 132.3, 130.0, 128.9, 128.3, 127.8, 108.4, 16.4. GC-MS: 218 ($M^+$).

14b: $^1$H-NMR (300 MHz, $CDCl_3$): 11.5 (bs, 1H), 7.75 (dd, J=1.2 and 8.4 Hz, 2H), 7.63 (dd, J=2.1 and 7.2 Hz, 1H), 7.51-7.45 (m, 2H), 7.38-7.28 (m, 3H), 7.19-7.08 (m, 2H). $^{13}$C-NMR (75 MHz, $CDCl_3$): 165.3, 158.5, 146.3, 132.8, 132.7, 132.0, 131.7, 130.8, 130.4, 128.9, 128.7, 127.4, 126.8, 113.2. GC-MS: 314 ($M^+$).

14c: $^1$H-NMR (300 MHz, $CDCl_3$): 11.68 (bs, 1H), 8.17-7.15 (m, 10H). $^{13}$C-NMR (75 MHz, $CDCl_3$): 171.3, 165.3, 160.1, 148.3, 135.9, 133.5, 133.1, 133.0, 131.7, 131.1, 130.3, 130.2, 130.1, 129.5, 129.3, 128.9, 128.4, 127.8, 124.9, 122.9, 109.3. GC-MS: 360, 358 ($M^+$).

14d: $^1$H-NMR (300 MHz, $CDCl_3$): 10.34 (bs, 1H), 7.90 (m, 2H), 7.67-7.41 (m, 7H), 7.20 (s, 1H). $^{13}$C-NMR (75 MHz, $CDCl_3$): 164.9, 158.7, 149.1, 133.1, 133.0, 131.83, 131.79, 129.0, 127.6, 127.4, 122.1, 108.5. GC-MS: 358, 360 ($M^+$).

14e: $^1$H-NMR (300 MHz, $CDCl_3$): 10.19 (bs, 1H), 7.90 (m, 2H), 7.77 (t, J=1.8 Hz, 1H), 7.66-7.56 (m, 2H), 7.49-7.44 (m, 1H), 7.32-7.26 (m, 2H), 7.20 (s, 1H). $^{13}$C-NMR (75 MHz, $CDCl_3$): 164.8, 158.5, 148.7, 135.9, 134.7, 133.0, 131.8, 130.0, 129.0, 128.0, 127.4, 126.2, 124.1, 109.1. GC-MS: 314 ($M^+$).

14f: $^1$H-NMR (300 MHz, $CDCl_3$): 10.08 (bs, 1H), 8.24 (s, 2H), 7.93 (m, 2H), 7.77 (s, 1H), 7.60 (m, 1H), 7.51-7.45 (m, 2H), 7.39 (s, 1H). $^{13}$C-NMR (75 MHz, $CDCl_3$): 165.0, 159.1, 147.3, 136.3, 133.4, 132.5, 132.0, 131.7, 129.3, 127.6, 126.2, 125.3, 121.7, 110.9. GC-MS: 416 ($M^+$).

14g: 1.9 g, Yield: 51%. $^1$H-NMR (300 Hz, $CDCl_3$): 10.10 (1H, bs), 7.93 (2H, J=7.2 Hz, d), 7.59 (1H, m), 7.52-7.47 (2H, m), 7.13 (1H, s), 7.04 (2H, s), 3.92 (6H, s), 3.87 (3H, s). $^{13}$C-NMR (75 Hz, $CDCl_3$): 164.6, 158.1, 153.4, 150.0, 138.1, 133.0, 131.8, 130.0, 129.0, 127.3, 107.6, 103.3, 61.0, 56.2. MS-EI: 370 ($M^+$). HRMS (ESI(+)): Calcd. for $C_{19}H_{19}N_2O_4S$ (M+H): 371.1066. Found: 371.1052.

14h: $^1$H-NMR (300 MHz, $CDCl_3$): 8.20 (d, J=6.9 Hz, 2H), 8.09 (d, J=7.2 Hz, 2H), 7.62-7.43 (m, 6H), 2.51 (s, 2H). $^{13}$C-NMR (75 MHz, $CDCl_3$): 171.3, 165.2, 157.1, 144.4, 133.7, 133.3, 132.8, 131.9, 130.3, 130.1, 128.8, 128.4, 128.3, 128.1, 127.9, 122.0, 12.0. GC-MS: 294 ($M^+$).

14i: $^1$H-NMR (300 MHz, $CDCl_3$): 10.6 (bs, 1H), 7.82 (dd, J=1.2 and 8.1 Hz, 2H), 7.53-7.41 (m, 5H), 7.01 (m, 2H). $^{13}$C-NMR (75 MHz, $CDCl_3$): 164.7, 155.1, 144.2, 132.7, 132.0, 130.7, 130.0, 129.9, 128.8, 127.4, 122.2, 115.4, 115.2, 12.1. GC-MS: 312 ($M^+$).

14j: $^1$H-NMR (300 MHz, $CDCl_3$): 10.01 (bs, 1H), 7.92 (d, J=7.5 Hz, 2H), 7.69 (d, J=8.1 Hz, 2H), 7.57-7.45 (m, 3H), 7.19 (d, J=8.1 Hz, 2H), 7.14 (s, 1H), 2.37 (s, 3H). $^{13}$C-NMR (75 MHz, $CDCl_3$): 165.2, 158.9, 150.3, 137.9, 132.7, 131.9, 131.4, 129.4, 128.7, 127.4, 126.0, 107.3, 21.2. GC-MS: 294 ($M^+$).

14k: $^1$H-NMR (300 MHz, $CDCl_3$): 10.92 (bs, 1H), 7.80 (d, J=8.7 Hz, 2H), 7.10 (s, 1H), 6.94 (s, 2H), 6.84 (d, J=8.7 Hz, 2H), 3.86 (s, 6H), 3.84 (s, 3H), 3.83 (s, 3H). $^{13}$C-NMR (75 MHz, $CDCl_3$): 164.6, 163.1, 159.1, 153.2, 149.9, 137.9, 130.0, 129.4, 124.0, 114.0, 107.5, 103.3, 60.8, 56.0, 55.4.

14l: $^1$H-NMR (300 MHz, $CDCl_3$): 11.43 (bs, 1H), 7.73 (m, 2H), 7.30 (m, 2H), 7.12 (s, 1H), 6.88 (s, 2H), 3.85 (s, 6H), 3.83 (s, 3H). $^{13}$C-NMR (75 MHz, $CDCl_3$): 164.4, 159.0, 153.3, 150.1, 139.1, 138.0, 130.3, 129.7, 129.0, 128.8, 107.9, 103.3, 60.8, 56.0. GC-MS: 404 ($M^+$).

14m: $^1$H-NMR (300 MHz, $CDCl_3$): 11.07 (bs, 1H), 7.44 (dd, J=1.8 and 8.1 Hz, 1H), 7.39 (s, 1H), 7.11 (s, 1H), 6.92 (s, 2H), 6.78 (d, J=8.4 Hz, 1H), 3.92 (s, 3H), 3.86 (s, 6H), 3.83 (s, 3H), 3.82 (s, 3H). $^{13}$C-NMR (75 MHz, $CDCl_3$): 164.8, 159.2, 153.3, 152.8, 150.1, 148.9, 138.0, 129.9, 124.2, 120.8, 110.4, 110.3, 107.6, 103.3, 60.9, 56.0, 55.8. GC-MS: 430 ($M^+$).

14n: $^1$H-NMR (300 MHz, $CDCl_3$): 11.03 (bs, 1H), 8.28 (d, J=9.0 Hz, 1H), 7.10 (s, 2H), 7.09 (s, 1H), 6.68 (dd, J=2.1 and 9.0 Hz, 1H), 6.56 (d, J=2.1 Hz, 1H), 4.11 (s, 3H), 3.96 (s, 6H), 3.90 (s, 3H), 3.89 (s, 3H). $^{13}$C-NMR (75 MHz, $CDCl_3$): 164.8, 162.6, 159.2, 158.1, 153.4, 149.9, 138.0, 134.5, 130.4, 112.0, 107.5, 106.1, 103.4, 98.7, 60.9, 56.4, 56.2, 55.7.

14o: $^1$H-NMR (300 MHz, $CDCl_3$): 11.50 (bs, 1H), 7.13 (d, J=0.3 Hz, 1H), 7.06 (s, 2H), 6.90 (s, 2H), 3.87 (s, 3H), 3.84 (s, 6H), 3.82 (s, 3H), 3.78 (s, 6H). $^{13}$C-NMR (75 MHz, $CDCl_3$): 165.1, 159.3, 153.3, 153.1, 150.2, 141.9, 138.1, 129.6, 126.8, 107.8, 104.8, 103.2, 60.9, 60.8, 56.1, 56.0.

14p: $^1$H-NMR (300 MHz, $CDCl_3$): 11.38 (bs, 1H), 7.84 (dd, J=1.5 and 7.8 Hz, 1H), 7.24-7.15 (m, 3H), 7.12 (s, 2H), 4.11 (s, 3H), 3.96 (s, 6H), 3.92 (s, 3H), 3.89 (s, 3H). $^{13}$C-NMR (75 MHz, $CDCl_3$): 162.6, 157.5, 153.4, 152.6, 150.1, 148.0, 138.1, 130.3, 124.8, 124.0, 123.0, 117.0, 107.6, 103.4, 61.9, 60.9, 56.2.

14q: $^1$H-NMR (300 MHz, $CDCl_3$): 11.19 (bs, 1H), 8.33 (dd, J=1.5 and 7.8 Hz, 1H), 7.57 (dt, J=1.5 and Hz, 1H), 7.19-7.07 (m, 5H), 4.14 (s, 3H), 3.96 (s, 6H), 3.89 (s, 3H). $^{13}$C-NMR (75 MHz, $CDCl_3$): 162.7, 157.8, 157.7, 153.4, 150.0, 138.0, 134.5, 132.6, 130.3, 121.7, 119.0, 111.6, 107.7, 103.4, 60.9, 56.4, 56.2.

14r: ¹H-NMR (300 MHz, CDCl₃): 10.75 (bs, 1H), 7.41-7.39 (m, 2H), 7.31 (m, 1H), 7.12 (s, 1H), 7.05 (m, 1H), 6.96 (s, 2H), 3.88 (s, 6H), 3.84 (s, 3H), 3.77 (s, 3H). ¹³C-NMR (75 MHz, CDCl₃): 164.8, 159.8, 158.5, 153.3, 150.1, 138.0, 133.1, 129.9, 129.8, 119.4, 119.2, 112.2, 107.6, 103.3, 60.9, 56.0, 55.3.

General procedure for methylation of 14 (see FIG. 10). To a cooled mixture of NaH (0.26 g, 60% in oil, 6.5 mmol) in THF (20 mL) was added a solution of compound 14 (5 mmol) in THF (10 mL) dropwise. The mixture was warmed up to room temperature and stirred for 20 min. After that, the mixture was cooled to 0° C. again and MeI (6.5 mmol) was added dropwise. The mixture was then warmed up to room temperature and stirred for 2 h. Water (5 mL) was added to quench the reaction and the mixture was further diluted with water (50 mL). The mixture was extracted with CH₂Cl₂ (3×50 mL). The combined organic phase was dried with anhydrous MgSO₄. After removal of all the solvent, the residue was purified by silica gel chromatography (hexane/EtOAc=4:1) to afford product 15 (more polar) and 16 as solid.

15a: ¹H-NMR (300 MHz, CDCl₃): 7.83 (dd, J=1.8 and 7.8 Hz, 2H), 7.47-7.43 (m, 3H), 6.29 (d, J=1.2 Hz, 1H), 3.79 (s, 3H), 2.31 (d, J=1.2 Hz, 3H). ¹³C-NMR (75 MHz, CDCl₃): 174.0, 169.0, 137.1, 134.4, 131.3, 129.2, 128.0, 104.3, 32.9, 14.4. GC-MS: 232 (M⁺).

15b: ¹H-NMR (300 MHz, CDCl₃): 8.38 (dd, J=1.8 and 7.8 Hz, 2H), 7.54-7.39 (m, 7H), 6.60 (s, 1H), 3.63 (s, 3H). ¹³C-NMR (75 MHz, CDCl₃): 174.3, 168.4, 136.9, 136.3, 134.8, 132.3, 131.53, 131.49, 130.0, 129.9, 129.2, 128.1, 127.3, 108.1, 34.0. GC-MS: 328 (M⁺).

15c: ¹H-NMR (300 MHz, CDCl₃): 7.83 (dd, J=1.8 and 8.1 Hz, 2H), 7.64 (m, 1H), 7.59 (m, 1H), 7.51-7.36 (m, 6H), 6.60 (s, 1H), 3.75 (s, 3H). ¹³C-NMR (75 MHz, CDCl₃): 174.4, 168.9, 137.8, 136.8, 132.8, 132.5, 132.2, 131.6, 130.5, 129.3, 128.1, 127.8, 123.0, 107.8, 34.9. GC-MS: 374, 372 (M⁺).

15d: ¹H-NMR (300 MHz, CDCl₃): 8.37 (dd, J=1.5 and 8.1 Hz, 2H), 7.65 (d, J=6.6 Hz, 2H), 7.51-7.43 (m, 4H), 7.28 (d, J=7.2 Hz, 1H), 6.58 (d, J=0.9 Hz, 1H), 3.74 (d, J=2.1 Hz, 3H). ¹³C-NMR (75 MHz, CDCl₃): 174.3, 168.9, 138.2, 136.9, 132.3, 131.9, 131.6, 130.8, 129.5, 128.1, 124.2, 107.4, 34.9. GC-MS: 372, 374 (M⁺).

15e: ¹H-NMR (300 MHz, CDCl₃): 8.37 (d, J=7.8 Hz, 2H), 7.51-7.43 (m, 6H), 7.32 (m, 1H), 6.59 (s, 1H), 3.75 (s, 3H). ¹³C-NMR (75 MHz, CDCl₃): 174.4, 168.9, 137.9, 136.8, 135.0, 132.3, 131.6, 130.3, 129.9, 129.4, 129.3, 128.1, 127.4, 107.8, 34.9. GC-MS: 328 (M⁺).

15f: ¹H-NMR (300 MHz, CDCl₃): 8.37 (dd, J=1.5 and 8.1 Hz, 2H), 8.03 (s, 1H), 7.91 (s, 2H), 7.50-7.46 (m, 3H), 6.73 (s, 1H), 3.77 (s, 3H). ¹³C-NMR (75 MHz, CDCl₃): 174.4, 168.9, 136.4, 136.0, 132.8, 132.7, 132.4, 131.7, 129.2, 128.0, 123.3, 120.9, 109.4, 34.8. GC-MS: 430 (M⁺).

15g: 0.69 g, Yield: 36%. ¹H-NMR (300 Hz, CDCl₃): 8.37 (2H, J=7.8 Hz, d), 7.50-7.43 (3H, m), 6.60 (2H, s), 6.56 (1H, s), 3.92 (3H, s), 3.90 (6H, s), 3.76 (3H, s). ¹³C-NMR (75 Hz, CDCl₃): 174.3, 168.7, 153.5, 139.4, 139.1, 137.0, 131.5, 129.2, 128.1, 125.9, 106.7, 106.6, 61.0, 56.4, 35.0. MS-EI: 384 (M⁺). HRMS (ESI(+)): Calcd. for C₂₀H₂₁N₂O₄S (M+H): 385.1222. Found: 385.1214.

15h: ¹H-NMR (300 MHz, CDCl₃): 8.37 (dd, J=1.8 and 8.1 Hz, 2H), 7.53-7.42 (m, 6H), 7.33-7.30 (m, 2H), 3.61 (s, 3H), 2.17 (s, 3H). ¹³C-NMR (75 MHz, CDCl₃): 174.0, 167.0, 137.2, 134.1, 131.3, 130.4, 129.8, 129.5, 129.2, 129.1, 128.0, 117.8, 35.0. GC-MS: 308 (M⁺).

15i: ¹H-NMR (300 MHz, CDCl₃): 8.36 (dd, J=0.9 and 7.8 Hz, 2H), 7.47-7.44 (m, 3H), 7.32-7.22 (m, 4H), 3.60 (s, 3H), 2.15 (s, 3H). ¹³C-NMR (75 MHz, CDCl₃): 174.0, 167.0, 164.9, 161.6, 137.1, 133.0, 132.4, 132.2, 131.4, 129.2, 128.0, 125.74, 125.70, 118.2, 116.5, 116.2, 34.9, 12.2. GC-MS: 326 (M⁺).

15j: ¹H-NMR (300 MHz, CDCl₃): 8.38 (dd, J=1.5 and 7.8 Hz, 2H), 7.48-7.44 (m, 3H), 7.30 (s, 4H), 6.53 (s, 1H), 3.74 (s, 3H), 2.44 (s, 3H). ¹³C-NMR (75 MHz, CDCl₃): 174.2, 168.9, 139.8, 139.6, 137.1, 131.4, 129.6, 129.23, 129.17, 128.0, 127.7, 106.6, 34.9, 21.4. GC-MS: 308 (M⁺).

15k: ¹H-NMR (300 MHz, CDCl₃): 8.33 (d, J=9.0 Hz, 2H), 6.95 (d, J=9.0 Hz, 2H), 6.60 (s, 2H), 6.53 (s, 1H), 3.92 (s, 3H), 3.90 (s, 6H), 3.88 (s, 3H), 3.74 (s, 3H). ¹³C-NMR (75 MHz, CDCl₃): 173.9, 168.4, 162.4, 153.5, 139.2, 139.1, 131.1, 129.7, 126.0, 113.2, 106.6, 106.4, 61.0, 56.3, 55.3, 34.9, 29.7.

15l: ¹H-NMR (300 MHz, CDCl₃): 8.30 (d, J=8.7 Hz, 2H), 7.42 (d, J=8.7 Hz, 2H), 6.60 (s, 2H), 6.58 (s, 1H), 3.93 (s, 3H), 3.90 (s, 6H), 3.75 (s, 3H). ¹³C-NMR (75 MHz, CDCl₃): 173.2, 168.8, 153.6, 139.5, 139.3, 137.6, 135.5, 130.7, 128.3, 125.7, 106.8, 106.7, 61.0, 56.4, 35.0.

15m: ¹H-NMR (300 MHz, CDCl₃): 8.00 (m, 1H), 7.91 (m, 1H), 7.37 (t, J=7.8 Hz, 1H), 7.05 (m, 1H), 6.60 (s, 2H), 6.57 (s, 1H), 3.93 (s, 3H), 3.90 (s, 6H), 3.89 (s, 3H), 3.76 (s, 3H). ¹³C-NMR (75 MHz, CDCl₃): 174.1, 168.8, 159.5, 153.5, 139.4, 139.2, 138.5, 129.0, 125.8, 121.8, 118.0, 113.6, 106.7, 106.6, 61.0, 56.4, 55.4, 35.0.

15n: ¹H-NMR (300 MHz, CDCl₃): 8.35 (dd, J=1.8 and 7.8 Hz, 2H), 7.49-7.41 (m, 3H), 6.23 (d, J=1.2 Hz, 1H), 3.95 (s, 3H), 1.75 (m, 1H), 1.02 (m, 2H), 0.73 (m, 2H). ¹³C-NMR (75 MHz, CDCl₃): 174.0, 169.1, 140.6, 137.1, 131.3, 129.2, 128.0, 103.9, 33.2, 8.7, 5.9. GC-MS: 258 (M⁺).

15o: ¹H-NMR (300 MHz, CDCl₃): 7.68 (s, 2H), 6.61 (s, 2H), 6.57 (s, 1H), 3.96 (s, 6H), 3.93 (s, 3H), 3.92 (s, 3H), 3.91 (s, 6H), 3.77 (s, 3H). ¹³C-NMR (75 MHz, CDCl₃): 173.7, 168.8, 153.5, 152.7, 141.1, 139.4, 139.2, 132.3, 125.8, 106.7, 106.6, 106.4, 61.0, 60.9, 56.3, 56.1, 34.9.

16a: ¹H-NMR (300 MHz, CDCl₃): 7.97 (dd, J=1.8 and 7.8 Hz, 1H), 7.60-7.46 (m, 7H), 7.37-7.23 (m, 2H), 3.74 (s, 3H). ¹³C-NMR (75 MHz, CDCl₃): 170.4, 159.0, 146.0, 134.5, 133.5, 132.1, 131.3, 130.9, 130.6, 128.73, 128.66, 127.6, 126.9, 114.6, 38.5. GC-MS: 328 (M⁺).

16b: ¹H-NMR (300 MHz, CDCl₃): 8.1 (s, 1H), 7.83 (d, J=7.8 Hz, 1H), 7.59-7.44 (m, 6H), 7.31-7.28 (m, 2H), 3.76 (s, 3H). ¹³C-NMR (75 MHz, CDCl₃): 170.5, 160.2, 147.9, 136.7, 134.4, 131.0, 130.7, 130.2, 129.1, 128.7, 127.6, 124.5, 122.9, 110.2, 38.5. GC-MS: 374, 372 (M⁺).

16c: ¹H-NMR (300 MHz, CDCl₃): 7.80 (d, J=8.7 Hz, 2H), 7.59-7.50 (m, 7H), 3.75 (s, 3H). ¹³C-NMR (75 MHz, CDCl₃): 170.4, 160.2, 148.3, 134.5, 133.7, 131.8, 131.0, 128.7, 127.6, 121.8, 109.6, 38.5. GC-MS: 372, 374 (M⁺).

16d: 0.35 g, Yield: 18%. ¹H-NMR (CDCl₃): 7.61-7.57 (2H, m), 7.55-7.50 (3H, m), 7.19 (1H, s), 7.15 (2H, s), 3.95 (6H, s), 3.89 (3H, s), 3.77 (3H, s). ¹³C-NMR (CDCl₃): 170.4, 160.0, 153.5, 149.5, 138.3, 134.5, 131.0, 130.5, 128.7, 127.6, 108.9, 103.4, 61.0, 56.2, 38.5. MS-EI: 384 (M⁺). HRMS (ESI(+)): Calcd. for C₂₀H₂₁N₂O₄S (M+H): 385.1222. Found: 385.1211.

16e: ¹H-NMR (300 MHz, CDCl₃): 7.69-7.64 (m, 2H), 7.57-7.48 (m, 5H), 7.16-7.10 (m, 2H), 3.67 (s, 3H), 2.52 (s, 3H). ¹³C-NMR (75 MHz, CDCl₃): 170.2, 163.7, 160.5, 156.2, 143.8, 134.6, 131.6, 130.8, 130.1, 130.0, 128.6, 127.6, 123.3, 115.4, 115.1, 37.9, 12.1. GC-MS: 326 (M⁺).

16f: ¹H-NMR (300 MHz, CDCl₃): 7.82 (d, J=8.1 Hz, 2H), 7.59-7.49 (m, 5H), 7.24-7.19 (m, 3H), 3.76 (s, 3H), 2.39 (s, 3H). ¹³C-NMR (75 MHz, CDCl₃): 170.4, 159.9, 149.5, 137.7, 134.7, 132.0, 130.8, 129.4, 128.6, 127.6, 126.0, 108.4, 38.4, 21.3. GC-MS: 308 (M⁺).

16g: $^1$H-NMR (300 MHz, CDCl$_3$): 7.58 (d, J=8.4 Hz, 2H), 7.16 (s, 1H), 7.16 (s, 2H), 7.00 (d, J=8.7 Hz, 2H), 3.95 (s, 6H), 3.89 (s, 6H), 3.81 (s, 3H). $^{13}$C-NMR (75 MHz, CDCl$_3$): 170.2, 161.8, 160.4, 153.4, 149.2, 138.0, 130.6, 130.0, 126.4, 113.9, 108.7, 103.4, 60.9, 56.2, 55.4, 38.8, 29.7.

16h: $^1$H-NMR (300 MHz, CDCl$_3$): 7.23-7.17 (m, 3H), 7.16 (s, 2H), 6.95 (d, J=8.4 Hz, 1H), 3.96 (s, 3H), 3.95 (s, 6H), 3.93 (s, 3H), 3.88 (s, 3H), 3.82 (s, 3H). $^{13}$C-NMR (75 MHz, CDCl$_3$): 170.1, 160.4, 153.4, 151.4, 149.3, 149.0, 138.1, 130.5, 126.5, 121.3, 111.3, 110.4, 108.7, 103.4, 61.0, 56.2, 56.0, 38.8, 29.7. GC-MS: 444 (M$^+$).

16i: $^1$H-NMR (300 MHz, CDCl$_3$): 7.35 (d, J=8.4 Hz, 1H), 7.16 (s, 3H), 6.60 (dd, J=2.4 and 8.4 Hz, 1H), 6.52 (d, J=2.1 Hz, 1H), 3.94 (s, 6H), 3.88 (s, 3H), 3.87 (s, 3H), 3.84 (s, 3H), 3.64 (s, 3H). $^{13}$C-NMR (75 MHz, CDCl$_3$): 168.9, 162.8, 159.9, 157.1, 153.4, 149.0, 138.0, 130.7, 129.9, 117.2, 108.5, 105.0, 103.4, 98.5, 60.9, 56.2, 55.6, 55.5, 36.7.

16j: $^1$H-NMR (300 MHz, CDCl$_3$): 7.19 (s, 1H), 7.16 (s, 2H), 6.82 (s, 2H), 3.95 (s, 6H), 3.92 (s, 3H), 3.90 (s, 6H), 3.89 (s, 3H), 3.80 (s, 3H). $^{13}$C-NMR (75 MHz, CDCl$_3$): 170.1, 160.2, 153.5, 153.3, 149.4, 140.3, 138.2, 130.5, 129.5, 108.9, 105.1, 103.4, 61.01, 60.98, 56.3, 56.2, 38.7.

16k: $^1$H-NMR (300 MHz, CDCl$_3$): 7.20-7.18 (m, 2H), 7.15 (s, 2H), 7.05 (dd, J=1.5 and 8.1 Hz, 1H), 6.93 (dd, J=1.5 and 7.8 Hz, 1H), 3.95 (s, 6H), 3.93 (s, 3H), 3.88 (s, 3H), 3.86 (s, 3H), 3.63 (s, 3H). $^{13}$C-NMR (75 MHz, CDCl$_3$): 168.4, 159.4, 153.4, 152.7, 149.1, 145.2, 138.0, 130.5, 130.0, 124.9, 119.0, 114.0, 108.7, 103.4, 61.7, 60.9, 56.2, 55.9, 36.7.

16l: $^1$H-NMR (300 MHz, CDCl$_3$): 7.47 (m, 1H), 7.38 (dd, J=1.8 and 7.5 Hz, 1H), 7.18 (s, 1H), 7.16 (s, 2H), 7.08 (dt, J=0.9 and 7.5 Hz, 1H), 7.00 (d, J=8.4 Hz, 1H), 3.95 (s, 6H), 3.88 (s, 3H), 3.86 (s, 3H), 3.63 (s, 3H). $^{13}$C-NMR (75 MHz, CDCl$_3$): 168.9, 155.5, 153.4, 149.1, 138.0, 131.7, 130.6, 128.3, 124.5, 121.1, 111.0, 108.7, 103.4, 60.9, 56.2, 55.6, 36.5.

16m: $^1$H-NMR (300 MHz, CDCl$_3$): 7.41 (m, 1H), 7.19 (s, 1H), 7.15 (s, 2H), 7.15-7.05 (m, 3H), 3.95 (s, 6H), 3.89 (s, 3H), 3.86 (s, 3H), 3.76 (s, 3H). $^{13}$C-NMR (75 MHz, CDCl$_3$): 170.2, 159.7, 153.4, 149.3, 138.1, 135.7, 130.5, 129.8, 119.5, 116.8, 112.8, 108.9, 103.4, 60.9, 56.2, 55.4, 38.4.

The additional thiazole compounds were synthesized and tested for antimigration efficacy and cytotoxicity, with results shown in TABLE 3.

TABLE 3

| Thiazole compound | IC$_{50}$ (anti-migration, µM) | Cytotoxicity (Survival at 1 µM) |
| --- | --- | --- |
| 5l | 5.56 | 141.8% |
| 5m | 0.176 | 85.0% |
| 5n | 0.333 | 70.4% |
| 5o | 0.087 | 90.0% |
| 5p | 0.032 | 109.5% |
| 5q | 0.242 | 115.3% |
| 5r | 11.0 | 70.2% |
| 6 | 0.000 | 106.4% |
| 7a | 0.565 | 68.5% |
| 7b | 0.432 | 100.0% |
| 7c | 0.0243 | 64.8% |
| 7d | 0.0647 | 63.0% |
| 8a | 0.883 | 128.9% |
| 8b | 0.0324 | 116.0% |
| 10 | 11 | 137.4% |
| 11 | 1.46 | 92.4% |
| 12 | >25 | 116.7% |
| 14a | 12 | 103.1% |
| 14b | 15 | 102.4% |
| 14c | 10 | 78.0% |
| 14d | 9.5 | 82.2% |
| 14e | 0.123 | 71.4% |
| 14f | 0.336 | 85.8% |
| 14g | >50 | 95.0% |
| 14h | >25 | 99.0% |
| 14i | 9.1 | 53.7% |
| 14j | 0.308 | 55.6% |
| 14k | >25 | 93.8% |
| 14l | >25 | 85.6% |
| 14m | >25 | 87.3% |
| 14n | >50 | 93.8% |
| 14o | 1.03 | 77.6% |
| 14p | 15 | 90.1% |
| 14q | 8.5 | 103.7% |
| 14r | 14 | 92.6% |
| 15a | 15 | 102.6% |
| 15b | 0.268 | 72.2% |
| 15c | 0.300 | 94.4% |
| 15d | 0.125 | 59.3% |
| 15e | 0.367 | 35.2% |
| 15f | 0.096 | 79.8% |
| 15g | 1.07 | 88.4% |
| 15h | 0.197 | 68.4% |
| 15i | 0.847 | 83.8% |
| 15j | >25 | 112.6% |
| 15k | 8.0 | 105.6% |
| 15l | 0.758 | 77.6% |
| 15m | >50 | 103.5% |
| 15n | 0.104 | 90.7% |
| 15o | 1.96 | 81.5% |
| 16a | 0.0416 | 88.9% |
| 16b | 0.437 | 104.4% |
| 16c | 0.317 | 65.4% |
| 16d | 10 | 96.4% |
| 16e | 1.62 | 107.6% |
| 16f | 1.09 | 59.3% |
| 16g | 0.312 | 100.0% |
| 16h | >25 | 101.9% |
| 16i | 5.04 | 118.5% |
| 16j | 0.470 | 114.8% |
| 16k | 0.108 | 117.6% |
| 16l | >25 | 109.3% |
| 16m | 0.646 | 88.9% |

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A compound of Formula (I)

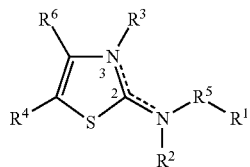
(I)

wherein
- R¹ is phenyl;
- R² is absent;
- R³ is ethyl, n-propyl, n-butyl, n-hexyl, n-dodecyl, allyl, or propynyl;
- R⁴ is hydrogen;
- R⁵ is —C(=O)—;
- R⁶ is phenyl or xylyl; and
- the dashed lines represent optional double bonds;

and wherein
the optional double bond between the amino nitrogen and position 2 of the thiazole ring is present;

or a salt thereof;

or a compound of formula 5k:

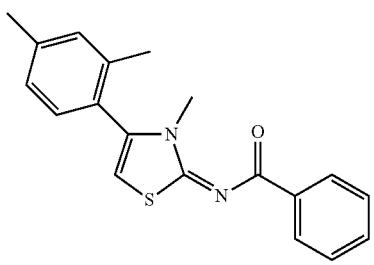
(5k)

or a salt thereof.

2. The compound of claim 1, wherein said compound is formula 5l:

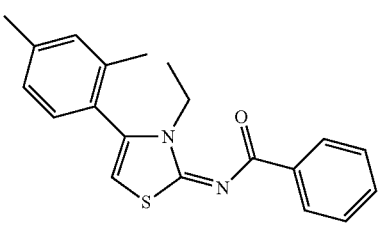
(5l)

or a salt thereof.

3. The compound of claim 1, wherein said compound is formula 5m:

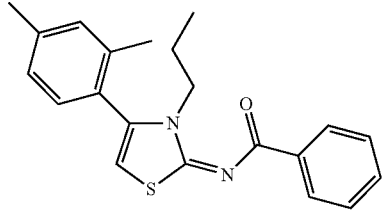
(5m)

or a salt thereof.

4. The compound of claim 1, wherein said compound is formula 5n:

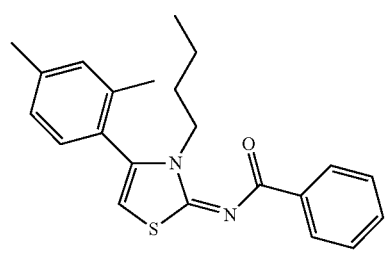
(5n)

or a salt thereof.

5. The compound of claim 1, wherein said compound is formula 5o:

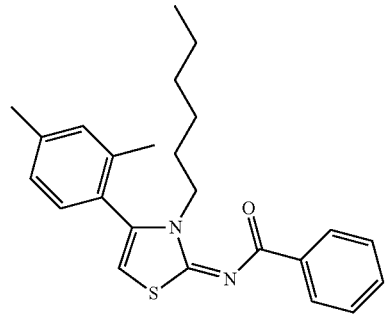
(5o)

or a salt thereof.

6. The compound of claim 1, wherein said compound is formula 5p:

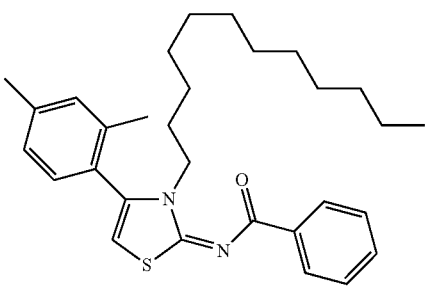
(5p)

or a salt thereof.

7. The compound of claim 1, wherein said compound is formula 5q:

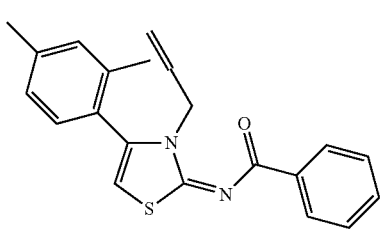

(5q)

or a salt thereof.

8. The compound of claim 1, wherein said compound is formula 5r:

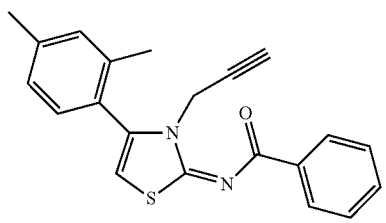

(5r)

or a salt thereof.

9. The compound of claim 1, wherein said compound is formula 7b:

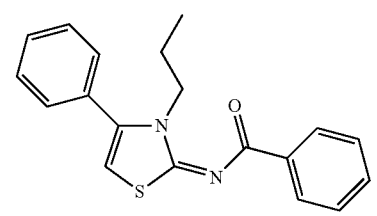

(7b)

or a salt thereof.

10. The compound of claim 1, wherein said compound is formula 7c:

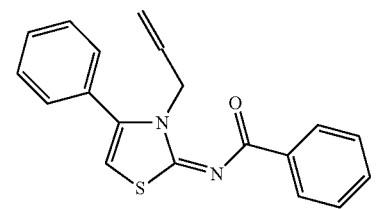

(7c)

or a salt thereof.

11. The compound of claim 1, wherein said compound is formula 7d:

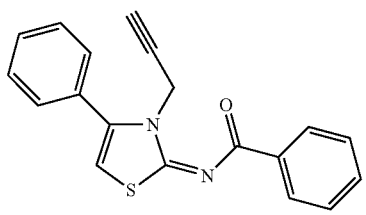

(7d)

or a salt thereof.

12. The compound of claim 1, wherein said compound is formula 8a:

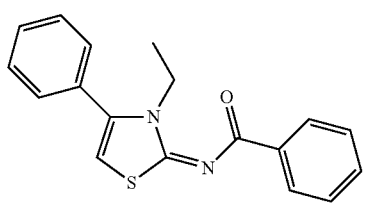

(8a)

or a salt thereof.

13. A method of treating a cancer selected from the group consisting of metastatic cancer, breast cancer and non-small cell lung cancer, in a mammal in need thereof, the method comprising administering to the mammal a composition comprising the compound of claim 1.

14. A method of inhibiting cell migration in a mammal with metastatic cancer, breast cancer or non-small cell lung cancer, the method comprising administering to the mammal a composition comprising the compound of claim 1.

15. A method of inhibiting cell invasion in a mammal with metastatic cancer, breast cancer or non-small cell lung cancer, the method comprising administering to the mammal a composition comprising the compound of claim 1.

16. A composition comprising the compound of claim 1, wherein said composition is in a form of a product for oral delivery, said product form being selected from the group consisting of a concentrate, dried powder, liquid, capsule, pellet, and pill.

17. A composition comprising the compound of claim 1, wherein said composition is in a form of a product for parenteral, intravenous, intradermal, intramuscular, or subcutaneous administration.

18. A composition comprising the compound of claim 1, further comprising at least one carrier, binder, diluent, or excipient.

19. A composition comprising the compound of claim 1, further comprising a chemotherapeutic agent.

20. The method of claim 13, wherein said compound is administered at from about 0.01 to about 40 mg/kg/day.

* * * * *

UNITED STATES PATENT AND TRADEMARK OFFICE
CERTIFICATE OF CORRECTION

PATENT NO. : 9,650,369 B2  
APPLICATION NO. : 14/431789  
DATED : May 16, 2017  
INVENTOR(S) : Guangdi Wang et al.

Page 1 of 1

It is certified that error appears in the above-identified patent and that said Letters Patent is hereby corrected as shown below:

In the Specification

At Column 1, Lines 14-18, please add the following replacement paragraphs:
-- STATEMENT REGARDING FEDERALLY SPONSORED RESEARCH OR DEVELOPMENT
This Invention was made with U.S. Government support under Contract No. 5G12RR026260 awarded by the National Institutes of Health. The Government has certain rights in this invention. --

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*